US011839499B2

(12) United States Patent
Zurovcik

(10) Patent No.: US 11,839,499 B2
(45) Date of Patent: Dec. 12, 2023

(54) PACKAGING SYSTEM WITH FOLDED SIDEWALLS

(71) Applicant: Worldwide Innovative Healthcare, Inc., Cambridge, MA (US)

(72) Inventor: Danielle R. Zurovcik, Cambridge, MA (US)

(73) Assignee: Worldwide Innovative Healthcare, Inc., Cambridge, MA (US)

( * ) Notice: Subject to any disclaimer, the term of this patent is extended or adjusted under 35 U.S.C. 154(b) by 398 days.

(21) Appl. No.: 16/615,750

(22) PCT Filed: May 22, 2018

(86) PCT No.: PCT/US2018/033985
§ 371 (c)(1),
(2) Date: Nov. 21, 2019

(87) PCT Pub. No.: WO2018/217827
PCT Pub. Date: Nov. 29, 2018

(65) Prior Publication Data
US 2020/0107901 A1 Apr. 9, 2020

Related U.S. Application Data

(60) Provisional application No. 62/509,430, filed on May 22, 2017.

(51) Int. Cl.
*A61B 50/30* (2016.01)
*B65D 5/42* (2006.01)
*B65D 5/50* (2006.01)

(52) U.S. Cl.
CPC ............ *A61B 50/30* (2016.02); *B65D 5/4204* (2013.01); *B65D 5/4233* (2013.01); *B65D 5/5007* (2013.01); *A61B 2050/3008* (2016.02)

(58) Field of Classification Search
CPC .. B65D 5/5007; B65D 5/4204; B65D 5/4233; B65D 5/5002; B65D 5/50; B65D 25/10; B65D 25/101; A61B 50/30; A61B 2050/3008
USPC .................................................. 206/570, 438
See application file for complete search history.

(56) References Cited

U.S. PATENT DOCUMENTS

| | | | | |
|---|---|---|---|---|
| 5,299,734 A * | 4/1994 | Lane | ..................... | B65D 5/5007 229/161 |
| 5,358,116 A * | 10/1994 | Brintazzoli | .......... | B65D 5/5061 206/443 |
| 5,361,907 A * | 11/1994 | Mohrhauser | ......... | B65D 5/5021 206/443 |
| 7,401,703 B2 * | 7/2008 | McMichael | ............ | A61B 50/33 206/370 |
| 7,604,119 B2 * | 10/2009 | Schott | .................... | B65D 85/38 206/454 |
| 7,905,355 B2 * | 3/2011 | Williams-Hartman | ...................... | B65D 75/36 206/532 |
| 2008/0093246 A1 * | 4/2008 | Duchamp | .............. | B65D 85/38 210/646 |

(Continued)

*Primary Examiner* — Steven A. Reynolds
(74) *Attorney, Agent, or Firm* — Douglas Denninger

(57) ABSTRACT

A packaging system utilizing a thin, planar sheet of material that is folded to have a base and at least three sidewalls. At least one mounting feature is integrated into at least one sidewall to secure at least one medical device component, wherein the at least one medical device component is mountable onto the at least one sidewall.

27 Claims, 16 Drawing Sheets

(56) References Cited

U.S. PATENT DOCUMENTS

2015/0313912 A1\* 11/2015 Karandikar .......... A61K 9/7007
514/184

\* cited by examiner

| Component | No. | Label |
|---|---|---|
| Forceps | 2 | 1a |
| Cotton Swab | 2 | 1b |
| Ruler | 1 | 1c |
| Saline Container | 1 | 1d&6c |
| Sealant Container | 1 | 6a |
| Sealant Applicator | 1 | 6b |
| Drape | 1 | 2 |
| Gauze Sponge | 6 | 1e |
| Drainage Tube | 1 | 3 |
| Pump Cap | 1 | 4 |
| Bellows Pump | 1 | 5 |
| Leur Lock Cap | 1 | 9 |
| Powder Stickpack | 1 | 10 |
| Wound Label | 1 | 11 |
| Instructions Label | 1 | 0 |
FIG. 1
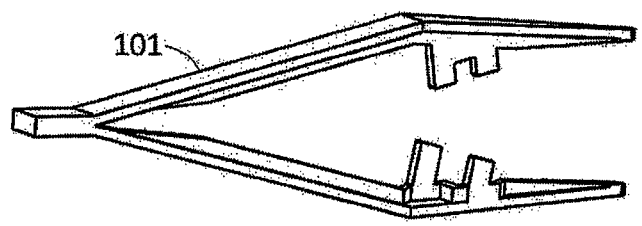
FIG. 2
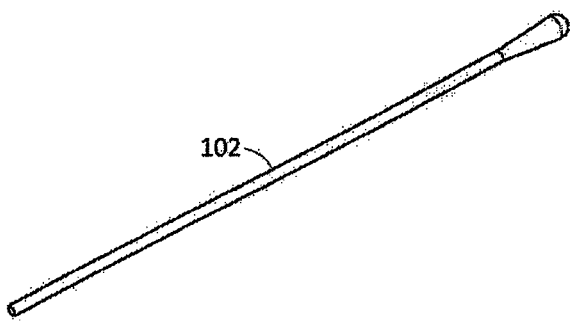
FIG. 3

PACKAGING SYSTEM WITH FOLDED SIDEWALLS

CROSS-REFERENCE TO RELATED APPLICATION

This application claims priority to U.S. Provisional Application No. 62/509,430 filed on 22 May 2017 by the present inventor. The entire contents of the above-mentioned application are incorporated herein by reference.

FIELD OF THE INVENTION

This invention relates to packaging systems for medical devices, and more particularly to mounting card packaging systems for the marketing, distribution, storage, and use of medical devices.

BACKGROUND OF THE INVENTION

Medical devices are commonplace in the treatment of patients. They are often an essential component in providing care. They include surgical instruments, implants, prostheses, therapeutic devices, including for wound therapy and physical therapy, drainage devices, including chest tubes, wound drains, and their corresponding pumps, diagnostic devices to diagnose various diseases, such as thermometers, test strips, and rapid diagnostic test (RDT) devices, test devices, such as for a pulmonary breathing test, wearables, including insulin pumps, heart monitors, sleep apnea masks, and some breast pumps. Surgical instruments are medical devices that assist a surgical team in performing an operation. They include forceps, scalpels, trocars, syringes, catheters, sutures, staplers, drills and drill bits, saws, drivers, endoscopes, mixers to combine multiple fluid and/or gas components, and retractors. Casts, splints, strapping, prostheses, external fixations, and some wound therapies are typically external devices attached to the body and used to assist and/or heal compromised structures of the body, although a small portion of a fixation may be internal. Wearables and many physical therapy devices, such as sequential compression devices (SCDs), are also external devices attached to the body and may be removed. By comparison, implants can be used for various treatments and are often more permanent. They include devices to treat compromised hard and soft tissues and/or certain disease states, such as cardiovascular implants, including pace makers, ventricular assist devices (VADs), stents, heart valves, and annuloplasty rings, orthopedic implants, such as bone screws, plates, and joint replacements, dental implants, and brain shunts. Furthermore, beyond the number of types of devices, each device may have multiple designs that may span across multiple manufacturers. Medical kits, such as a suture kit with multiple devices, are also considered to be medical devices herein.

Medical devices are typically regulated by a governing body, in order to protect the patients treated in the corresponding governed territory; this often includes the oversight of the medical device packaging as well. In the regulatory process, devices are typically divided into categories and/or classes, which in turn determine the oversight of the regulatory body. These device groups may reflect the level of risk of the devices in each group and, therefore, oversight may increase with increased risk. Some examples of regulatory bodies include: Food and Drug Administration (FDA) in the United States; European Medicines Agency (EMA) in the European Union; Pharmaceuticals and Medical Devices Agency (PMDA) in Japan; Central Drugs Standard Control Organization (CDSCO) in India; National Health Surveillance Agency (ANVISA) in Brazil; and China Food and Drug Administration (CFDA) in China. The regulatory body may assure that the medical device, its components, and their packaging are meeting the necessary requirements for safe treatment, by requiring specific validation tests prior to device approval. In addition, the quality management system of a medical device manufacturer should provide guidelines and procedures to assure that the devices are safe and meet all necessary device and/or regulatory requirements.

Medical devices may be used in various care settings, including the operating room, intensive care unit (ICU), patient hospital bed, outpatient care setting (e.g., exam room), home, and field, such as a battlefield, disaster relief, or ambulatory care setting. Each setting and/or device may have different packaging requirements, including different marketing needs, sterilization process compatibility, impact force (e.g., shock and vibration) resistances, environmental conditions needed to be withstood during transport and storage, length of shelf-life, and/or level of sterility maintained during its shelf-life. In general, the minimum purpose of the medical device packaging system is to ensure that a safe, reliable, and fully functional device arrives at the point of end use. In many cases, this includes that the packaging maintains sterility of the device until the packaging is opened.

Many medical devices and/or specific device components must be sterilized prior to use in order to help to prevent infection of the patient. The sterilization of the medical device and/or at least one of its components may be done before, during, or after the closed packaging of the device and/or at least one of its components, which may produce at least one device and/or component that is sterilized and ready for use immediately upon removing the device and/or component from its closed packaging. Depending on the sterilization requirements, the device and/or its components may be packaged together or separately. In addition, there may be multiple, separate packages combined in one or more "main" packages. In this case, the packaging system containing the sterile device and/or at least one of its sterile components must be capable of maintaining the sterility of the device and/or its specific components throughout their shelf-lives. If the device and/or its components are packaged prior to sterilization, the packaging must allow adequate penetration of the sterilizing agent. Visual indicators may be present on the packaging that change color if the packaging is properly sterilized. However, these indicators may only indicate the initial sterilization process and may have no indication of the sterility overtime.

Currently, there are many packaging mechanisms that are used in medical device packaging, including: bags (including header bags and linear tear bags), pouches, trays (including rigid, semi-rigid, and flexible styles, which includes blister packs), lids, mounting cards, and folded cartons. These can be made of various materials and their combinations, along with various coatings, for example: bags (including form-fill-seal bags) may be made from nylon, PA, PE (e.g., HDPE, LDPE, and LLDPE), paper, Tyvek®, PVC, nylon, EVA and other polymers; pouches (including form-fill-seal pouches) may be made from nylon, paper, Tyvek®, Mylar, foil, PET, PE (e.g., HDPE, LDPE, and LLDPE), PVC, EVA, and other polymers; trays (including form-fill-seal trays) may be made from APET, PETG, PETG Foam, PET, nylon, EVA, ionomer, EVOH, PP, Aclar®, HIPS, PVC, PC, HDPE, PU, and other polymers; lids may be made from Tyvek®, paper, foil, PET, PE (e.g., HDPE and LLDPE), PA, nylon, and other polymers; mounting cards may be made from PETG, paperboard, including solid bleached sulfate (SBS), solid unbleached sulfate, clay coated new back, and solid fiber, styrene, HDPE, and other polymers and board materials; and folded cartons may be made from boxboard, cardboard, carton board, paperboard, vinyl, and other polymers and board materials.

Coatings and/or laminates may be added to the packaging materials, in order to achieve desired properties that are not inherent to the material. Packaging materials that are not inherently water resistant or water proof may be coated and/or laminated, in order to achieve the desired surface property. Coatings and/or laminates may also be added to protect the surface of the package from UV rays and external wear and tear, particularly if the package is printed, as printing can fade or rub off. Coatings and/or laminates may be internally or externally applied for protection against other internal and/or external environmental conditions, including temperature, humidity, and chemicals, including liquids and gases. Adhesives may be coated onto packaging components, so they can be adhered to other packaging, labeling, and/or device components. Coatings include, adhesives, waxes, animal proteins, aqueous solutions, varnishes, and UV coatings. Laminates include films of polypropylene, polyester, and nylon.

Packaging mechanisms may be used individually or in combination with each other. Typically, the number of packaging components used may increase with the complexity of the device, number of components, and/or their delicacy. Individual packaging component materials must be able to withstand any sterilization processes that they go through. This may also lead to multiple stages of packaging, using multiple packaging components. For example, one device component and its packaging may go through a sterilization process and then are subsequently combined into one package with additional device components and their potential corresponding packaging that went through a separate sterilization process and/or no sterilization process.

Bags and pouches are a very common flexible packaging option in the medical device industry. They typically include at least two layers secured together with a seal along a majority of the edges during their initial manufacture with an opening for placing a medical device therein. At least one of the layers may be a clear material, so that its contents can be seen. At least one material may be a material that enables sterilization to occur (e.g., enables ethylene oxide to pass through), such as Tyvek®. After the medical device is inserted, the opening may be sealed using calibrated heat sealing equipment. All of the seals may be such that any breaches in the seals are evident to a user so that proper procedures can be taken if the seals were compromised prior to opening the package. After completely sealed, the bag or pouch may then be sterilized. Typically, bags and pouches are used as sterile barriers, as material options allow for: 1) the flexible packaging to be easily sealed over multiple device and/or packaging component configurations; 2) the sealed packaging and its contents to be sterilized, including wet/steam sterilization, dry heat sterilization, hydrogen peroxide gas plasma and other low temperature oxidative sterilization, sporicidal chemical sterilization techniques, irradiation, electron beam, and ethylene oxide (EtO); and 3) the sealed packaging to maintain sterility of its contents during its predetermined shelf-life. To remove one or more medical device components from a pouch or bag, the end user typically pulls the layers of the pouch or bag apart from each other. However, other opening mechanisms may be included, such as tear strips and perforated tear lines when contents do not have sterility requirements. The bag or pouch is the only packaging component in the system in some constructions and, in other constructions, is used in combination with other components.

An alternative to bags and pouches, particularly for bulky devices with high volume manufacturing, are form-fill seal flexible trays that can be made with thin materials called bottom webs, such that they may be considered to be flexible packaging. These are a very common packaging option in the higher volume medical device industry, as the manufacturing process typically includes an automated thermoforming process with in-line automated and/or manual filling and sealing. This packaging option requires high upfront tooling costs and long set-up times. Devices such as syringes, bulb syringes, and bulb drains are often packaged with a form-fill seal flexible tray that is sealed with a lid. A lid is typically heat sealed to the entire border of the mouth of the container. Although the thin container material is flexible, the device inside often adds rigid volume to the package, and in some cases, the final, sealed packages may be stacked in different orientations to nest into each other and reduce the volume needed for shipping and storage. To open these containers, the user must peel the lid from the form-fill seal container.

If more rigid component protection is desired, semi-rigid trays are often used due to common design embodiments that offer easy loading and assembly. In addition, tray designs typically offer easy stackability, both before and after they are filled. Before they are filled, they can often nest into each other, allowing for minimal transport and storage volume requirements. However, once trays are filled, typically a lid is applied to seal the contents, and the end result is typically robust and stackable, but often bulky. A lid is typically heat sealed to the entire border of the mouth of the tray or container. In some cases, the final, sealed packages may be stacked in different orientations to nest into each other and reduce the volume needed for shipping and storage.

There are drawbacks to the semi-rigid trays, one of which is large taper angles necessary for easy part removal from the mold during their manufacturer. This may make the packaging footprint increasingly large, particularly if deep pockets are necessary in the package, in order to hold larger components. In addition, deeper pockets may require thicker materials, which may increase costs.

Various tray designs can overcome the drawbacks of increasing the vertical dimension. Clamshell designs may be used, in order to share the depth of the pocket between the two halves, and/or to create a pocket deep enough to constrain the component in the planar direction, which is then constrained along the vertical axis by the lid. One skilled in the art would also recognize that the clamshell design can be combined or replaced with other similar designs, such as a tray and separate domed lid. Both of these designs have drawbacks, as the clamshell lid may become cumbersome during use, as it flops about, and a separate domed lid must be disposed of or set aside, which may be cumbersome due to its potential size; these drawbacks may also cause the potential of breaking a sterile barrier. The clamshell and domed lid designs do not typically provide an occlusive, sealed volume around the device, and therefore, they can be used in combination with a bag or pouch around the outside. This is especially useful if the contents need to be sterilized.

Clamshell designs and designs with separate domed lids are also used, whereas the lid portion of each takes up the negative space of the tray/container portion. Typically, no additional vertical height is added beyond the thickness of the lid material around an edge lip. This allows the lid portion of the tray design to better restrain the components within the tray/container volume.

Nested (i.e., stackable and/or nested layers) trays are another design used to reduce the planar footprint of a tray. With this design, multiple trays are nested above one another, in order to use the vertical space above the footprint of the tray. This design method may be used if a large planar component needs to be kitted with additional components; sometimes a mounting card may be stacked in a tray to create multiple levels. This nested design can also be achieved with a form-fill seal tray serving as the outer tray. In general, this design has the same footprint drawbacks as the clamshell and domed lid designs when the components underneath need to be accessed. For easy access or component visualization, multiple tray/container levels may be set side-by-side in some cases, which multiples the space needed during its use. This is not ideal in many healthcare settings, where there is a small work area, typically on a cart or table that is bedside.

Device space is often shared with additional equipment, such as additional devices (e.g., gloves and surgical instruments) and saline bottles. Sometimes the medical device packaging is emptied onto a prefabricated sterile barrier field, and sometimes, if its outer surface is sterile, it is placed onto a prefabricated sterile barrier field, and in some cases, it serves as the sterile barrier field. The sterile field has limited space and may also be shared with additional equipment. Therefore, in general, packaging designs should try to maintain a minimum footprint.

Semi-rigid trays have additional drawbacks. They are bulky to dispose of, and if they are crushed down, sharp edges may form. This may cause them to poke through garbage bags or puncture medical gloves. In addition, they are typically made with a thermoforming process, which often requires high cost tooling and long set-up times.

Rigid trays (or other rigid packaging designs) are not common in medical device packaging, although they may offer robust protection, durability, and/or stackability. Typically, medical device packaging is disposed of, and therefore, the high costs of rigid packaging is preventative. Rigid trays may be made from an injection molding process, which typically has high tooling and process costs relative to the other packaging options. Their lids are typically hard plastic, and not the heat-sealed lids previously discussed. These lids may also be injection molded, and may be hinged to the bottom tray by-design. Foam may be used to take up any dead space in the internal volume, and/or to protect the device during shipping, storage, and/or handling. They are bulky to dispose of, and should not be crushed down, as they would form hard, sharp edges.

Mounting cards are currently not as frequently used in medical device packaging when compared to bags, pouches, trays, lids, and folded cartons. Mounting cards are typically a planar, semi-rigid material that is used to securely hold single or multiple device components in a particular position, utilizing retention tabs, folds, straps, and other mounting mechanisms. Often, they are used as a method to protect flexible packaging barriers from being punctured by enclosed medical device components. They are also used to maintain medical device component positioning in flexible medical packaging, in order to provide for easy opening and use, such as to maintain the winding position of long catheters. For these reasons, they are often used in combination with flexible packaging systems, which may provide a sterile barrier. One or more device components and/or mounting cards may be placed in the flexible packaging component, which is subsequently sealed to provide a closed environment.

Mounting cards have many potential benefits, compared to other options. Since their original form is planar, they can be stacked for minimal volume during storage and transport. They can be more cost-effective and environmentally-friendly than their alternatives, and they often have lower tooling costs. They are typically made from a die-cutting process with flat materials and are often referred to as die-cut inserts or die-cut backer cards; however, at lower volumes, they may also be cut on a CAM table or other cutting system, including by-hand. The end product is typically a flat card that has retention mechanisms to lock in components, which may also include folds, to create wallet-like designs. Typically, these folds are parallel to each other, creating a clamshell-type/wallet-like design. This allows: more components to be fit onto a design within a specific footprint when folded; protection from the top and/or two opposing sides; and/or limited stackability, which is often not possible in flexible packaging without a semi-rigid tray. However, during use, the clamshell-type/wallet-like design must be unfolded open, more than multiplying the footprint of the packaging. This is not typically ideal due to space limitations in care settings.

Folded cartons may offer more rigidity to any of the prior packaging options, or in some cases may be used as the only packaging component. These cartons may add rigidity to flexible packaging, such as pouches and bags, as they can be placed into the carton for shipping, storage, and/or handling. Cartons also provide a means for easily and/or orderly stacking devices and/or their components during shipping, storage, and/or handling. Although cartons are often used in medical device packaging, they also have drawbacks. They produce more waste and may be bulky to dispose of, and if they are crushed down, sharp edges may form. They make the packaging system more bulky, taking up more volume during shipping, storage, and/or handling. They are typically made from board materials, which may produce particulate and may not be permitted in an operating room or other environmentally controlled settings. They add cost to the packaging system, for a component that typically has little to no functionality during the application and use of the medical device.

Further complicating medical device packaging, each care setting and/or device also has different instruction and/or labeling requirements. Some devices are complex and/or high risk and may require more detailed instructions and/or labeling. Also, the level of knowledge of the end user may vary, especially in a disaster relief setting, which might increase the need for the inclusion of more detailed instructions and/or labeling. However, this is not often the case in practice, particularly in disaster relief settings where many devices are donated that are not designed for field applications.

In order to reduce errors and for consistent medical practice, medical professionals may continue to use a specific device make and/or model, often designed and/or marketed for the care setting that they typically practice. With this, they do not have to spend extra time reading the instructions and entire labeling for every use, and, if applicable, they do not have to be retrained on its use. These time-saving details also apply to their medical team, which multiplies the time savings. These are the optimized time savings in theory; however, the time savings may start before the device is used by the medical professional for the first time, as instruction manuals and some non-essential labeling may never be looked at, as many medical professionals use the devices that they were trained on during their educational training. In this case, most information that is deemed important is passed down by word-of-mouth, which may originate from sales representatives and not necessarily instruction manuals or labeling.

This reluctance to introduce new devices into a medical practice and/or to review the latest instructions may lead to slow adoption of new technologies and/or device designs. It may also lead to cancelled surgeries or treatment or increased user errors if devices are not available and/or become discontinued and new devices must be used instead. Misuse is a high risk if the device has the same basic components as standard-of-care and/or previously used designs, but the instructions for it to function properly are different. In this case, the device may be operated in the same manner as prior designs, which may result in multiple negative effects, including harm to the patient, product failure, and failure to penetrate the market. There is a need to avoid medical device misuse, particularly in cases where predicate devices are being replaced with a device that has the basic componentry, but different instructions and/or labeling.

SUMMARY OF THE INVENTION

The present invention achieves a new mounting card design and loading mechanism that overcome some of the drawbacks of present mounting card designs, while providing unique functionality.

This invention features a packaging system utilizing a thin, planar sheet of material, also referred to herein as a mounting card, that is folded to have a base and at least three sidewalls. At least one mounting feature is integrated into at least one sidewall to secure at least one medical device component, wherein the at least one medical device component is mountable onto the at least one sidewall.

In some embodiments, additional features in the planar sheet, such as tabs and/or slots, temporarily hold at least one pair of adjacent sidewalls together. In certain embodiments, additional features temporarily hold at least every other adjacent sidewall together when viewed around the base in a clockwise or counterclockwise direction. In some embodiments, additional features temporarily hold every adjacent sidewall together.

In some embodiments, the mounting card packaging is suitable for at least one of NPWT (Negative Pressure Wound Therapy), wound cleaning, and chronic wound treatment. In some embodiments, the user disengages at least one feature to activate the packaging instructions and achieve a display layout wherein a plurality of medical device components are arranged in a selected order. In one embodiment, at least one lip is defined around at least a majority of the top border. In another embodiment, a plurality of components are mounted on the lip features. In one embodiment, at least one of the lip features are interlocked. In certain embodiments, a sheet of material such as CSR (Central Supply Room) wrap and/or a sterile barrier is placed around the folded mounting card to constrain it and provide additional structural support.

This invention further features a jig to hold the mounting card. In certain embodiments, the jig includes at least one protuberance to at least partially activate a mounting feature on the mounting card.

BRIEF DESCRIPTION OF THE DRAWINGS

In what follows, preferred embodiments of the invention are explained in more detail with reference to the drawings, in which:

FIG. 1 is a schematic view of a component key, with the first column providing the component descriptive name, the second column providing the quantity of each component found in the kit, and the third column lists the label (reference number) of the component on the subsequent Figures herein, and which corresponds to its numerical instruction on the instruction label (0), shown in FIG. 16;

FIG. 2 is a schematic perspective view of a pair of forceps;

FIG. 3 is a schematic perspective view of a cotton swab;

DETAILED DESCRIPTION OF THE PRESENTLY PREFERRED EMBODIMENTS

Figure 4:
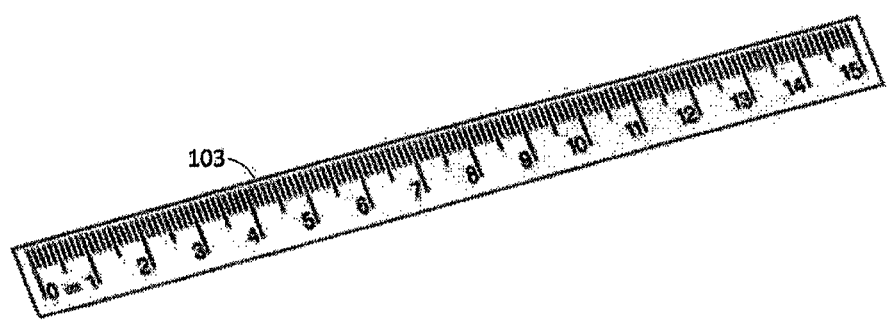
FIG. 4 is a schematic perspective view of a ruler.

This invention may be accomplished by a packaging system, which may also be considered as a packaging and loading mechanism system, utilizing a thin, planar sheet of preferably rigid material that is folded to have a base and at least three sidewalls. At least one mounting feature is integrated into a least one sidewall to secure at least one medical device component, wherein the at least one medical device component is mountable onto the at least one sidewall. Preferably, additional features in the planar sheet such as tabs and/or slots temporarily hold at least one pair of adjacent sidewalls together; more preferably, additional features temporarily hold at least every other adjacent sidewall together when viewed around the base in a clockwise or counterclockwise direction; and more preferably, additional features temporarily hold every adjacent sidewall together.

Medical device packaging systems according to the present invention preferably provide one or more of the following advantages:
 easy to incorporate multiple components of varying shapes and sizes;
 easy component loading during assembly;
 applicable to use with a jig during component loading;
 applicable to use with a jig during packaging assembly;
 easy to use and/or manipulate during assembly;
 easy assembly process by-hand;
 easy to automate assembly process;
 protective barrier that prevents the device from getting damaged during shipping, storage, and/or handling;
 capable of passing validation for shipping and storage requirements;
 sterile barrier that can be sterilized with its contents;
 sterile barrier that maintains sterility throughout the desired shelf-life of at least one enclosed medical device component;
 capable of passing sterilization validation;
 capable of preserving its contents throughout its shelf-life;
 protective barrier in expected environmental conditions;
 protective barrier in harsh environments;
 capable of passing shelf-life validation;
 easy to use and/or manipulate during medical procedure, including "no-touch" deployment without contacting device components;
 intuitive instructions for the end user to easily follow;
 easily accessible, intuitive instructions that complement the instructions for use (IFU) and other device labeling;
 easily accessible, intuitive instructions that reduce the need to reference the IFU and/or other labeling to achieve proper device functionality;
 minimized packaging volume;
 minimized packaging footprint;
 minimized medical device footprint during medical procedure;
 organized medical device components during its application and/or use;
 ergonomic;
 reduced packaging waste that meets any applicable medical waste and/or waste reduction standards, guidelines, and/or requirements; and
 low cost.

DISCLAIMER: NOTHING HEREIN SHALL BE INTERPRETED AS SEEKING TO AVOID ANY APPLICABLE REGULATORY REQUIREMENTS FOR PREPARING AND/OR USING MEDICAL DEVICES AND PACKAGING THEREFOR. IT IS THE RESPONSIBILITY OF EACH USER TO COMPLY WITH APPLICABLE REQUIREMENTS.

Figure 5:
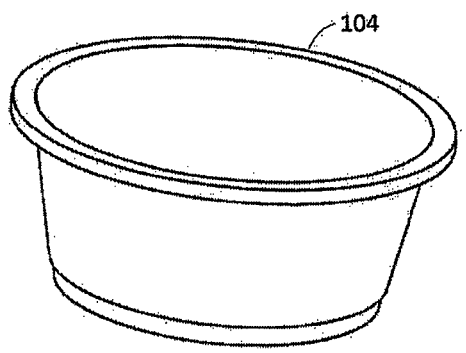
FIG. 5 is a schematic perspective view of a container for saline, Dakin's solution, Ringer's solution, or other liquid useful during a surgical or medical procedure.
Figure 6:
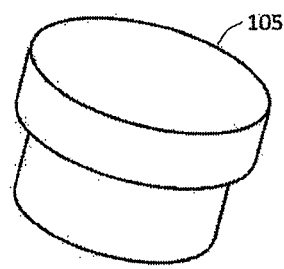
FIG. 6 is a schematic perspective view of a container for a sealant.
Figure 7:
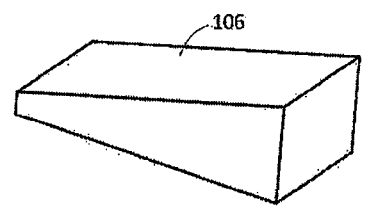
FIG. 7 is a schematic perspective view of a sealant applicator.
Figure 8:
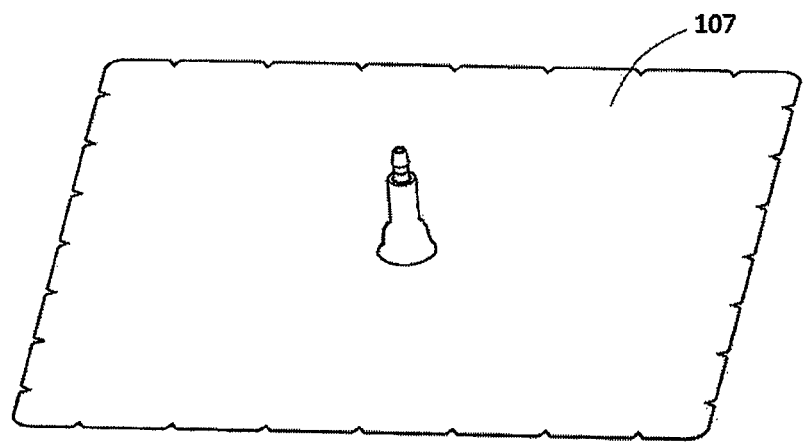
FIG. 8 is a schematic perspective view of a drape suitable for NPWT.
Figure 9:
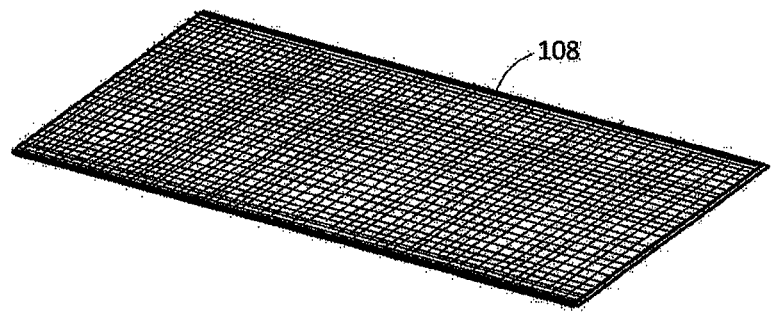
FIG. 9 is a schematic perspective view of a sheet of gauze useful as a sponge.
Figure 10:
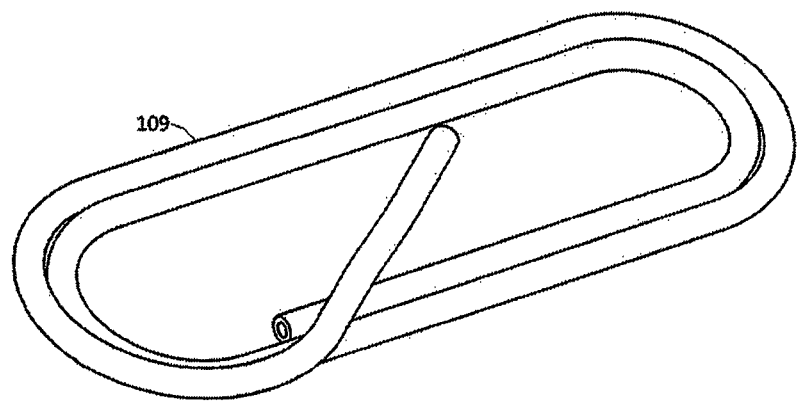
FIG. 10 is a schematic perspective view of a tube useful in NPWT.
Figure 11:
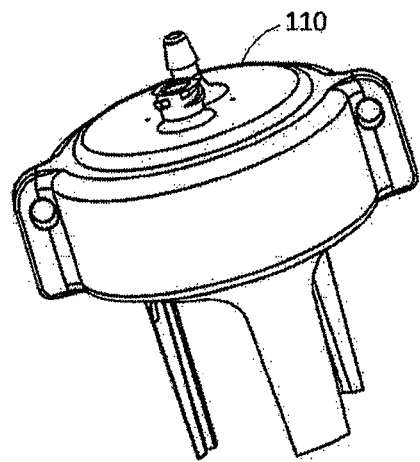
FIG. 11 is a schematic perspective view of a cap for a mechanical pump.
Figure 12:
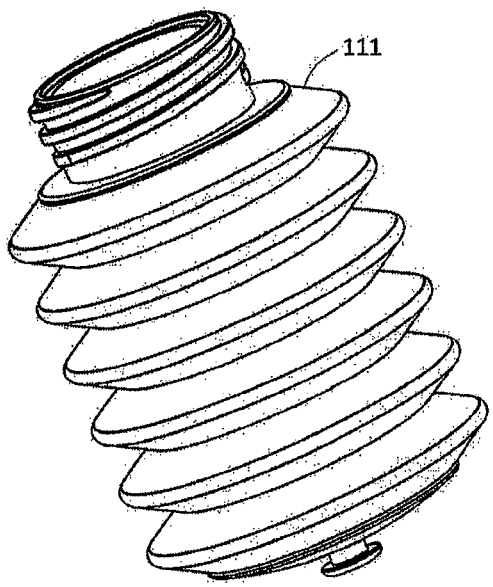
FIG. 12 is a schematic perspective view of a mechanical bellows pump.
Figure 13:
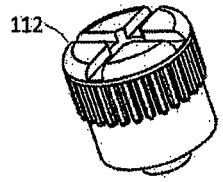
FIG. 13 is a schematic perspective view of a threaded male luer lock cap, representing a syringe-related component which typically mates with a catheter port or other tube-luer connection.
Figure 14:
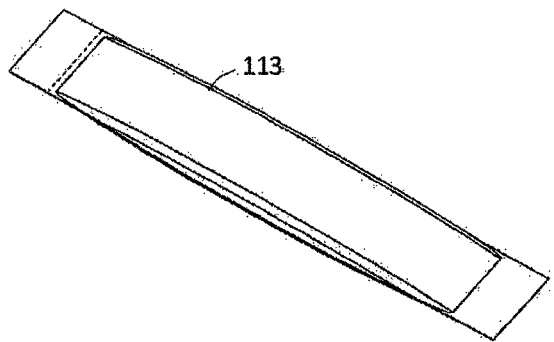
FIG. 14 is a schematic perspective view of a powder stick-pack, representing dry packaged material.
Figure 15:
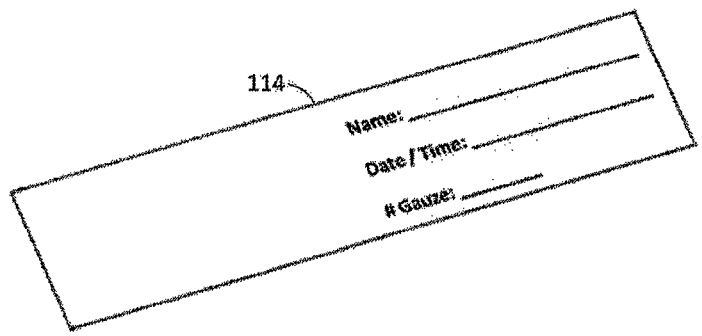
FIG. 15 is a schematic perspective view of a label on which healthcare-related information can be marked and placed near a wound and/or on wound therapy device components.
Figure 21:
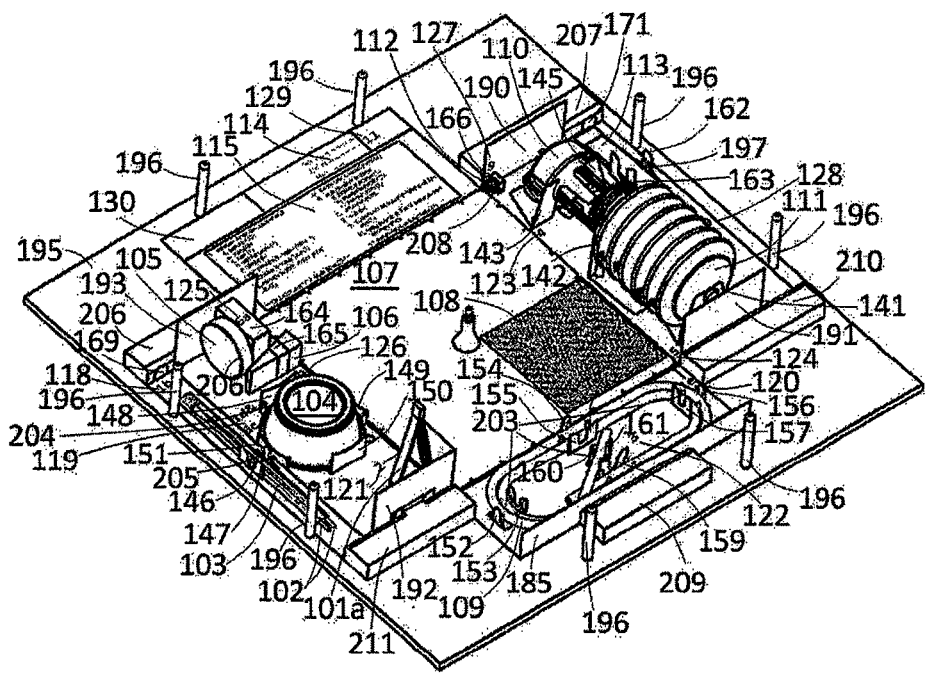
FIG. 21 is a schematic perspective view of components shown in FIGS. 2-16 mounted onto the mounting card and jig combination of FIG. 20 as a package according to the present invention.
Figure 22:
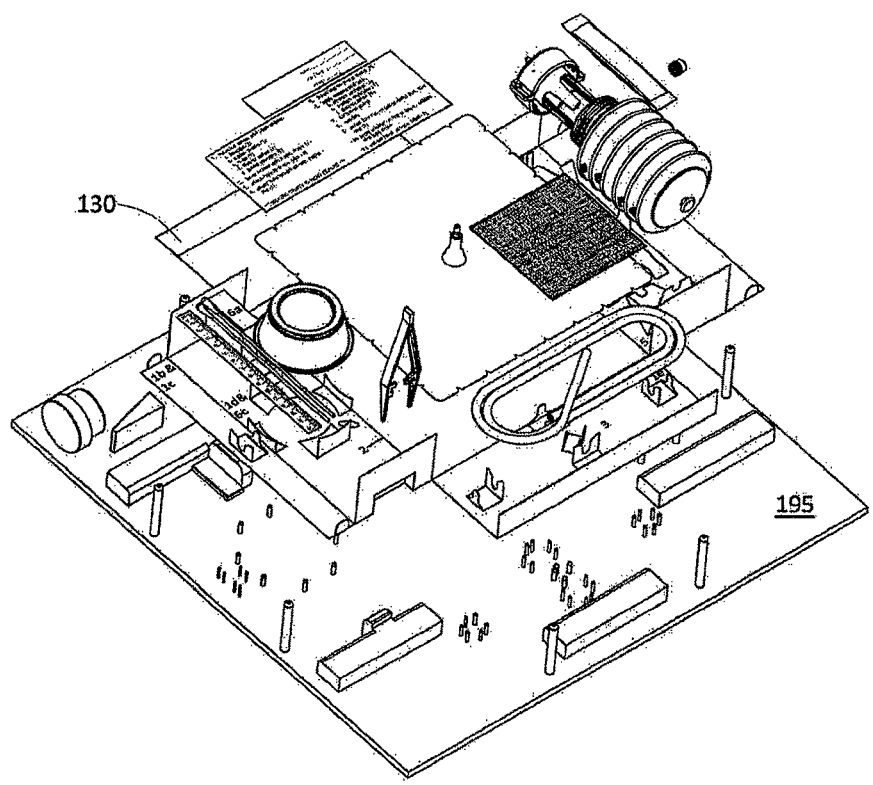
FIG. 22 is an exploded view of FIG. 21.

The novel packaging system disclosed in the present patent application is an ideal design for a kitted medical device with multiple components of varying shapes and sizes. As an illustrative example to explain the present packaging invention, packaging is disclosed for a novel mechanical negative pressure wound therapy (NPWT) kit, which incorporates multiple kit components, including those from the mechanical negative pressure wound therapy (NPWT) device kit described by the present inventor in U.S. Pat. No. 9,173,777 B2. The kit includes components listed in FIG. 1 and further detailed in FIGS. 2 through 16. In FIG. 1, the first column is the component descriptive name, the second column is the quantity of each component found in the kit, and the third column is the label (i.e., reference number) of the component, which corresponds to its numerical instruction on the instruction label 147 of FIG. 16 and any numerical component labels 116 through 129 on the packaging of FIGS. 17D, 18C, and 21 (116 is not visible in FIGS. 21, and 117 is not visible in FIGS. 18C and 21). The individual components include: forceps 101 of FIG. 2 (i.e., also 101a (numerical component label 117) and 101b, in subsequent figures), cotton swab 102 of FIG. 3 (numerical component label 118), ruler 103 of FIG. 4 (numerical component label 118), saline container 104 of FIG. 5 (numerical component label 119), sealant container 105 of FIG. 6 (numerical component label 125), sealant applicator 106 of FIG. 7 (numerical component label 126), drape 107 of FIG. 8 (numerical component label 121), gauze sponge 108 of FIG. 9 (numerical component label 120), drainage tube 109 of FIG. 10 (numerical component label 122) which may also be referred to as tubing, pump cap 110 of FIG. 11 (numerical component label 123), bellows pump 111 of FIG. 12 (numerical component label 124), luer lock cap 112 of FIG. 13 (numerical component label 127), powder stickpack 113 of FIG. 14 (numerical component label 128), wound label 114 of FIG. 15 (numerical component label 129), and instructions label 115 of FIG. 16 (numerical component label 116). The novel mounting card 130 design example used to kit these components is shown in FIGS. 17A, 17C, and 17D, which will be used as an example in further explaining concepts and details in this patent application. This example is not meant to narrow and/or limit the scope of the invention.

The novel mounting card package design disclosed in the present application can be easily stackable in its final packaging configuration and has the reduced planar footprint benefits of a multi-level nested tray. However, unlike nested trays and in a preferred embodiment, the present mounting card package does not require the removal of any separate packaging components in order to access any device component. In another embodiment according to the present invention, a nested concept may be utilized. The footprint of packaging according to the present invention typically is decreased relative to conventional packaging, while providing easy usability and enhanced product display characteristics. To yield these benefits, the card has folding lines 131 through 134 of FIG. 17A, that outline a central, flat surface, otherwise known as the base 135 of FIG. 17A. When folded, these folds create sidewalls 136, 137, 138, and 139 of FIGS. 17A and 24A to a central, enclosed volume 140 of FIG. 24A. Therefore, there must be a minimum of three sidewalls to form an enclosed volume. Preferably, the sidewalls are folded by 45 degrees to 135 degrees; more preferably, at least one sidewall is folded by 60 degrees to 120 degrees; even more preferably, at least one sidewall is folded by 80 degrees to 100 degrees. In at least one preferred embodiment, all of the sidewalls are folded by approximately 90 degrees; this is shown for the NPWT packaging example in FIG. 24A and FIG. 24B. The term "approximately" as utilized herein is defined to include variations up to ten percent (+/−10%).

It should be noted that folding lines in the mounting card can be scored on one or both sides and/or perforated. As the scores get deeper and/or the perforations longer, the folding line becomes more flexible. These techniques should be considered with the desired function of the folding line over its useful life. Scoring and/or perforating the folding lines 136 through 139 of the sidewalls may be preferable in making them easier to fold and/or manipulate during assembly. In certain constructions, one or more of the folds created according to the present invention can be referred to as a living hinge.

The folded mounting card configuration has a similar form of a semi-rigid tray. However, unlike trays (including form-fill seal trays), features 141 through 167 of FIG. 17A on the sidewalls can exist for mounting at least one device component. The present invention preferably includes at least one feature on at least one of the sidewalls to mount at least one device component that, in the preferable embodiment, is held in the enclosed internal volume 140 of the packaging design in its final packaging configuration. Suitable mounting features include retention tabs 141 through 145, retention folds 146 through 163, retention straps 164 through 166, hybrids of these features, and other similar and/or custom features that can provide constraint 167.

Figure 18A:
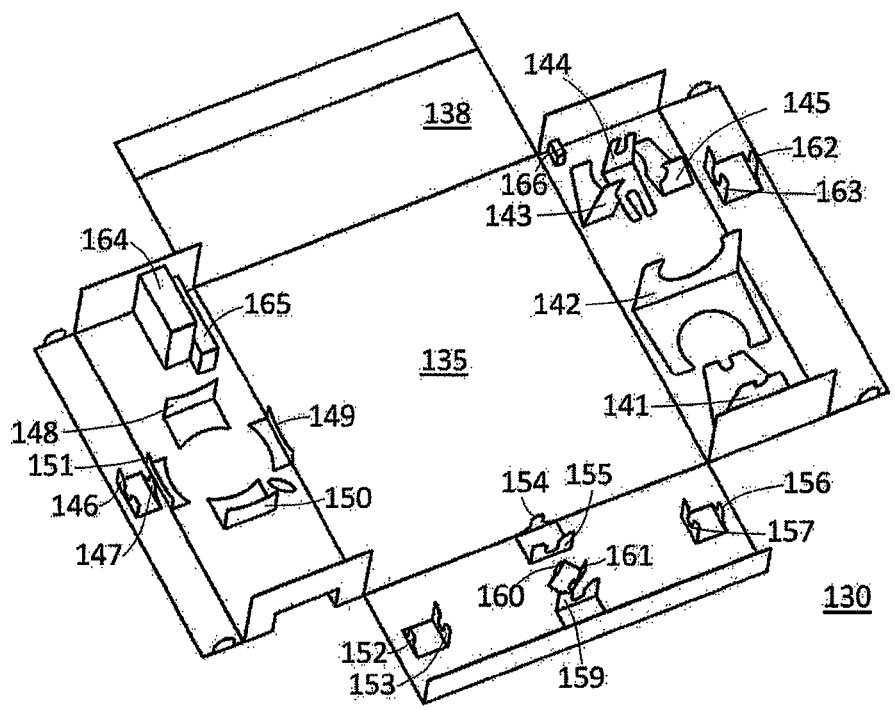
FIGS. 18A-18B are schematic perspective views of the mounting card of FIGS. 17A and 17C with mounting features raised.
Figure 23:
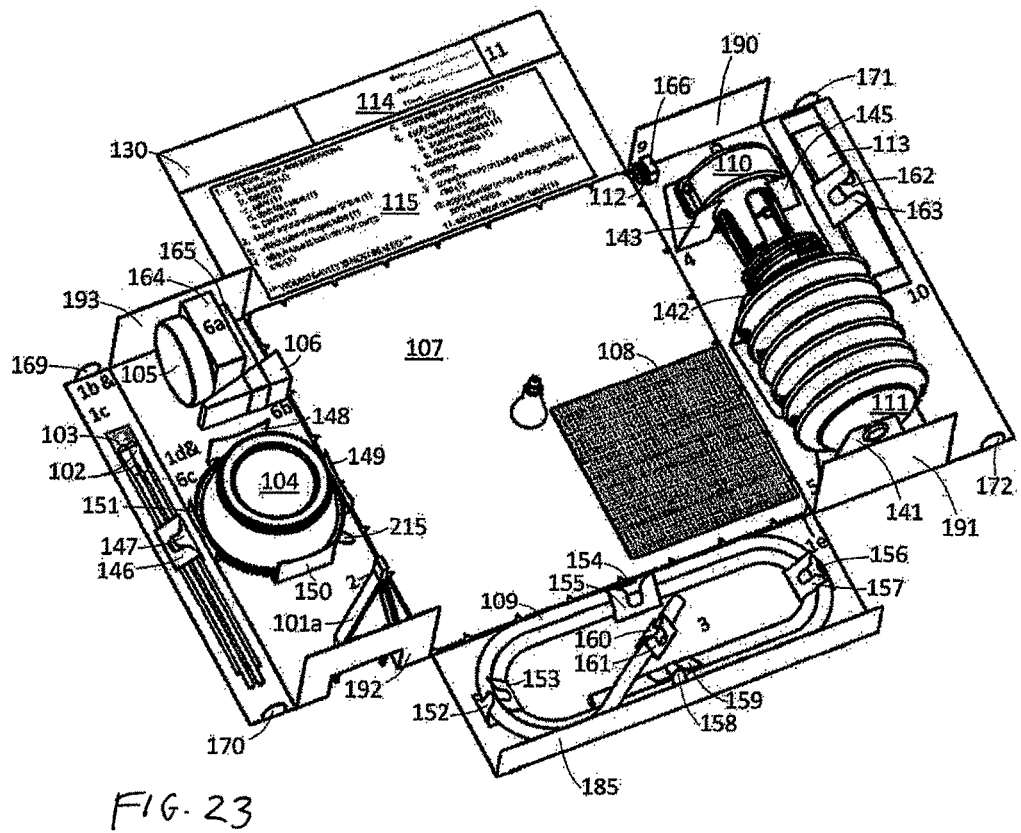
FIG. 23 is a schematic perspective view of the package of FIG. 21 removed from the jig.

As defined for this application, a retention tab 141 through 145 is a feature in the mounting card that can temporarily constrain and/or lock-in at least one feature of its corresponding device component(s) with one or more features in the tab. At least one retention tab is used to provide the desired constraint(s) to each corresponding component feature. As shown in FIGS. 18A and 23, in one embodiment, one tab provides the desired constraint, such as 141, 142, and 144, and in another embodiment, two or more tabs provide the desired constraint, such as 143 and 145.

Retention tabs 141 through 145 are typically die cut features that fold towards the component to be constrained (in the final packaging position of the component). A preferred tab feature may have the same or slightly smaller dimensions of the part of the component to be constrained, such that the retention tab fully contacts at least one part of the component feature and/or holds the component feature in-place with an interference fit. As an example shown in FIGS. 18A and 23, the diameter of the retention feature in tab 142, may be equal to or slightly smaller than the diameter of the neck of the bellows pump 111 that it constrains, and as another example, the diameter of the retention feature formed by tabs 143 and 145, may be equal to or slightly smaller than the diameter of the region of the pump cap 110 that it constrains. The interference fit in at least one preferred embodiment is a standard press fit design with its corresponding tolerances (for example, one potential standard is H7/p6 for holes and shafts under ISO 286-1). If the constrained component is soft, then the dimensional difference (s) in the interference fit may be larger, although damage to the component should be avoided. For instance, if a plastic flexible tube is compressed too tight in a retention tab feature, permanent kinks can form over the shelf-life of the device due to creep in the material. Any component damage should be avoided in the packaging design, particularly if it negatively affects the device performance.

In at least one embodiment, the tab features may be slightly larger than the dimensions of the part of the component to be constrained. This may be the case for reasons that include: if at least of one the dimensions of the component has wide tolerances that need to be accounted for, if the manufacturing process of the mounting card has large tolerances that need to be accounted for, if the component will be damaged by the forces of an interference fit, if other retention features further constrain the component to at least an acceptable level, and/or if the component is robust enough that a loose fit is deemed sufficient.

In at least one preferred embodiment, the retention tab feature includes a mouth for the insertion and removal of at least one corresponding component. The mouth of a flat retention tab may be oriented at any angle in the plane of the tab. The orientation of the mouth may be a part of the retention feature design in providing the necessary constraints to a component. For example, the mouths of three or more aligned, planar retention tabs can point in alternating directions (such as in alternating directions parallel to the plane of the unfolded mounting card), and then, a solid component can be woven between them for constraint. In at least one preferred embodiment, the insertion axes of all mouths point at least +/−45 degrees from the vertical axis (i.e., the axis perpendicular to the plane of the unfolded mounting card), more preferably +/−10 degrees, and even more preferably, +/−1 degree. This may allow for the components to be easily loaded from the vertical direction, especially in cases where automation is used. In the case of vertical assembly, any paths between the mouths and the final component positioning would ideally be straight paths, preferably within +/−10 degrees, more preferably within +/−5 degrees, and even more preferably within +/−1 degree along the insertion axis of the mouth, which may allow for faster assembly times. In general, the insertion path does not need to be straight and/or aligned with the insertion axis of the mouth, that is, the insertion path can be non-linear, which may enhance the constraint of a retention tab feature. For example, the path may be in the shape of a "U" or "G" where the tab feature mouth is at one end of the line and the final position of the component is at the other end. This non-linear and/or multi-directional path may provide better protection against the dislodgement of the device component from a tab feature during shipping, storage, and/or handling, although, in general, shorter, less complex paths may be more preferable for faster assembly times.

The preferred width of the mouth of a corresponding retention tab feature provides the necessary constraint in order for the retention tab feature to function properly. In at least one preferred embodiment, the mouth of the feature is part of the functional constraint of at least one device component, such that a removal force is necessary to remove the component through the mouth of the retention feature. In at least one embodiment, it is desirable for the width of the mouth to be smaller than the largest dimension of the width of the component feature to pass through the mouth. This is often the case when a circular component cross-section must be constrained by the retention feature, as shown in the example in FIGS. 18A and 23, whereas retention tab features of the tabs 141, 142, 143, and 145 constrain component features with circular cross-sections and tab 144 constrains two vertically aligned component features with circular cross-sections. For tab 144, the width of the mouth must be smaller than the diameter of the top feature that is to be constrained. These design examples require an assembly insertion force for at least one of the retention tab features, in order to push the corresponding component in-place and a removal force to remove the component from at least one of the retention tab features, such that the feature is otherwise locked into the retention feature.

The greater the dimensional difference between the mouth and the largest dimension of the component feature that must pass through the mouth, the higher the required assembly force and/or removal force. Depending on the required assembly force, the mouth of the retention feature may have at least one lead-in feature to assist with assembly and potentially reduce the assembly force. These lead-in features may include rounded corners 168 of FIG. 17A and/or chamfers on at least one entrance surface of the mouth of the retention feature. The dimensional differences also require a removal force with the same correlation as the insertion (i.e., assembly) force. In the preferred embodiment, the retention features are designed such that the necessary removal force will not be achieved until the device is being unpacked for use. Depending on the required removal force, the mouth of the retention feature may have at least one lead-out feature to assist with removal and potentially reduce the removal force. These lead-out features may include rounded corners 168 of FIG. 17A and/or chamfers on at least one exit surface of the mouth of the retention feature.

Scoring and/or perforating the folding lines of the retention tabs may be preferable in making them easier to fold during assembly; however, the depth of the scoring(s) and/or length of the perforation should be considered. Some designs rely on the stiffness of the folding line to maintain a force on at least one component. These forces may be used to increase the overall constraint stiffness. The magnitude of the force is typically the highest in the direction perpendicular to the flat surface of the retention tab. Therefore, if a pair of retention tabs that hold different features of one component fold from the card in opposite directions from one another, more component stability may be achieved, due to a resulting compression or tension force. For instance, a tab pair may apply an additional compressive force on a component that they are constraining, in the case that the pair of tabs fold away from each other, such as tabs 141 and 142 in FIGS. 18A and 23. This compression force can also be applied with more than two tabs, such as tabs 143, 144 and 145 in FIGS. 18A and 23. This force can be reduced or eliminated by further weakening the folding line with score lines and/or perforations. In general, the retention tabs should be designed such that they perform their appropriate function(s) throughout their useful life.

As defined for this application, a retention fold 146 through 163 is a feature in the mounting card that can temporarily constrain at least one area of its corresponding device component(s), by holding the area between itself and a second surface, being either the surface of the mounting card and/or another surface, such as the surface of a device component. Retention folds are typically die cut features that rely on the stiffness of the fold to apply a holding force to at least one device component between the fold and the second surface. The magnitude of the applied force is typically highest, perpendicular to the flat surface of the fold. The necessary holding force depends on the size and weight of the corresponding component(s), along with the forces that need to be withstood during the useful life of the packaging. In order to increase the holding force, the design of the folds can be manipulated, including the design of its folding line (e.g., increasing its length, decreasing perforation sizes, and/or decreasing score line depths), and/or at least one more retention fold may be added to the design, in order to hold the corresponding device component(s) that require a higher retention force. Increasing the length of the folding line will increase the stiffness of the fold and its corresponding holding force; the change in stiffness is linearly proportional to the length. Increasing the scoring depth and/or the lengths of the perforations along the folding lines will make the folds more flexible and their corresponding retention force less in magnitude; for score lines, the change in stiffness is proportional to the thickness cubed. Therefore, if a significant increase in stiffness is necessary to increase the holding force and no score lines or significant perforation lengths were used, different retention designs should be considered beyond a basic retention fold.

Figure 18B:
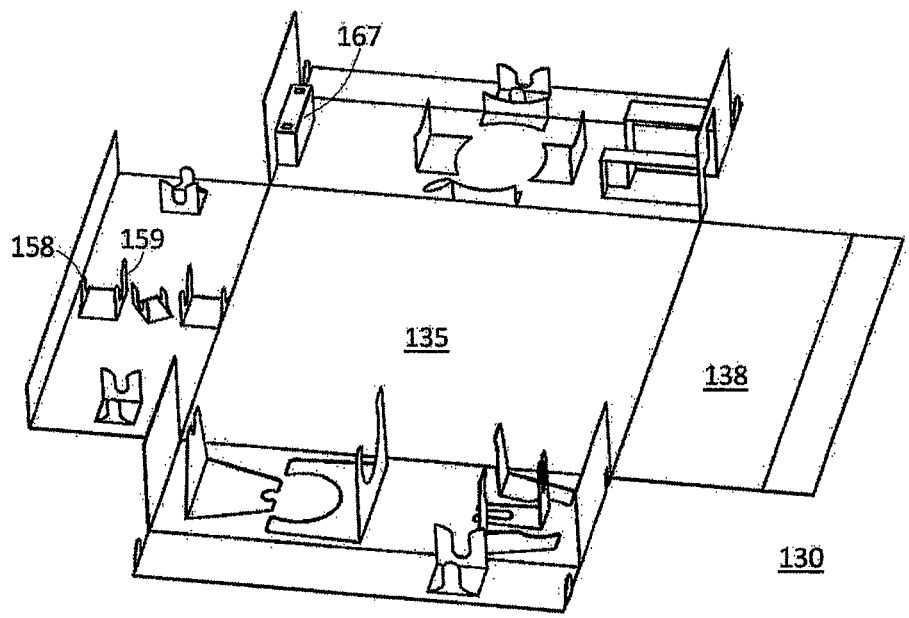

Multiple retention folds may also interlock with each other, in order to physically lock-in at least one part of at least one corresponding device component, which may produce a potential increase in constraint. This includes at least two retention folds that are side-by-side, folding in alternating directions, or at least two nested retention folds, such as folds 146 and 147, 152 and 153, 154 and 155, 156 and 157, 158 and 159, 160 and 161, and 162 and 163 in FIGS. 18A, 18B and 23, that fold in opposite directions and can apply retention forces into the region between them. Multiple retention folds may be arranged in other geometrical configurations, in order to hold at least one part of at least one component in-place. In one embodiment, multiple retention folds can be arranged in a circular pattern, in order to hold at least one circular device component or part of a device component between them, such as folds 148, 149, 150, and 151 in FIGS. 18A and 23, which hold the saline container 104 along its brim. In this embodiment, all folds may unfold along a folding line that is perpendicular to the radius of device component. This generates retention forces from the folds that point into the region between them. In general, a folding line that is perpendicular to the radius of the part of the device component that the retention fold contacts typically can generate higher holding forces.

As defined for this application, a retention strap 164, 165 and 166, as shown in the example in FIGS. 18A and 23, is a feature in the mounting card that wraps around at least one part of at least one component for constraint. A retention strap may have permanent or semi-permanent geometry and/or length, and/or may be adjustable in geometry and/or length. In the case where a strap is permanent or semi-permanent in geometry and/or length, as in straps 164, 165 and 166, the strap may constrain at least one part of at least one component through an interference fit. The interference fit in at least one preferred embodiment is a standard press fit design with its corresponding tolerances. If the constrained component is soft, then the dimensional difference(s) in the interference fit may be larger, although damage to the component should be avoided. For semi-permanent geometry, as in straps 164, 165 and 166, the flexibility of the strap material and/or design can create more flexible interference fits with lower assembly forces. For increased flexibility, scoring and/or perforation techniques may be used in at least one direction and/or length along the length of the strap, and/or other design features may be used including variations in the width of the strap, at least one cutout in the strap along its length, and/or at least one folding line across the strap.

If adjustable in geometry, the retention strap must be flexible enough and/or properly designed to achieve the final desired geometry. This may be done with material selection and/or the design, including scoring and/or perforation techniques in at least one direction and/or length, variations in the width of the strap, at least one cutout in the strap along its length, and/or at least one folding line across the strap. If adjustable in length, the retention strap may incorporate this length flexibility into its design. In one embodiment, the strap feature is permanently attached to the mounting card at one end, with holes at its opposite end. When in use, the strap can constrain at least part of at least one component by wrapping around it from the permanently fixed end, and subsequently attaching to a feature on the mounting card, including another strap feature, through one of the holes on the opposite end. This embodiment may be adjusted similar to a belt for pants. Therefore, the attachment hole selected will determine the tightness of the strap constraint. Tighter constraint may be necessary for heavier components and/or to withstand higher forces during the useful life of the packaging.

The belt design may also be adjustable to any length, instead of discrete lengths determined by the prefabricated holes. This may be preferable in the case that one packaging design is used across multiple products or if varying sizes of at least one corresponding secured part of at least one component may be included in the package. Techniques to secure the free end of the strap include: the strap may be pulled through an interference fit on the mounting card, and/or it may be woven through multiple slots or holes in the mounting card. With these techniques, the strap length is secured by friction. If a higher coefficient of friction is desirable on at least one of the contact surfaces, then, various techniques may be used to increase it. Potential techniques include: at least one contact surface may be machined by processes including scoring or grinding, a surface texture can be stamped into at least one contact surface, including along the border of any through holes (this may be incorporated directly into any through hole features on the die), and/or materials with a higher coefficient of friction may be used.

The belt design can also be implemented for the case of a fixed length strap design, where only one hole exists in the strap. This may make the assembly of the components easier, as the strap may be easier to manipulate during assembly. For both the adjustable and non-adjustable straps, the belt design concept also allows the strap to be woven through features of the medical device component(s), which may provide a preferable constraint option and/or increase the stability of the constraint. For both the adjustable and non-adjustable straps, the attachment point of the free end of at least one retention strap may also be onto at least one feature of at least one medical device component. In this case, this design would entail a custom variation of a retention strap design.

The retention (i.e., mounting) features listed above provide constraint mechanisms needed to hold and protect medical device components during shipping, storage, and/or handling. One or more mounting features may be required to provide the necessary constraint(s) for each component. In addition, one mounting feature may provide at least one constraint to one or more components.

In some packaging embodiments, mounting features are on at least two of the sidewalls to mount at least one component that, in the preferred embodiment, rests in the enclosed internal volume 140 of the design in its final packaging configuration, and in some embodiments, these features are on at least three of the sidewalls to mount at least one component.

Figure 24A:
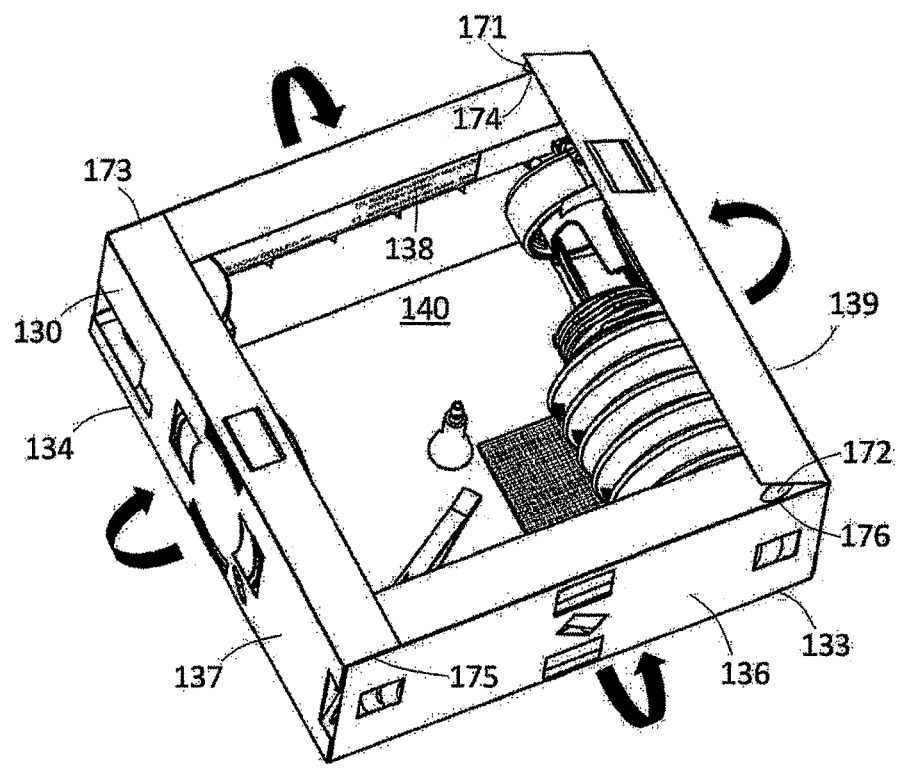
FIGS. 24A-24B are schematic perspective views of folding sidewalls and lips of the package of FIG. 23 to form an assembled package.
Figure 24B:
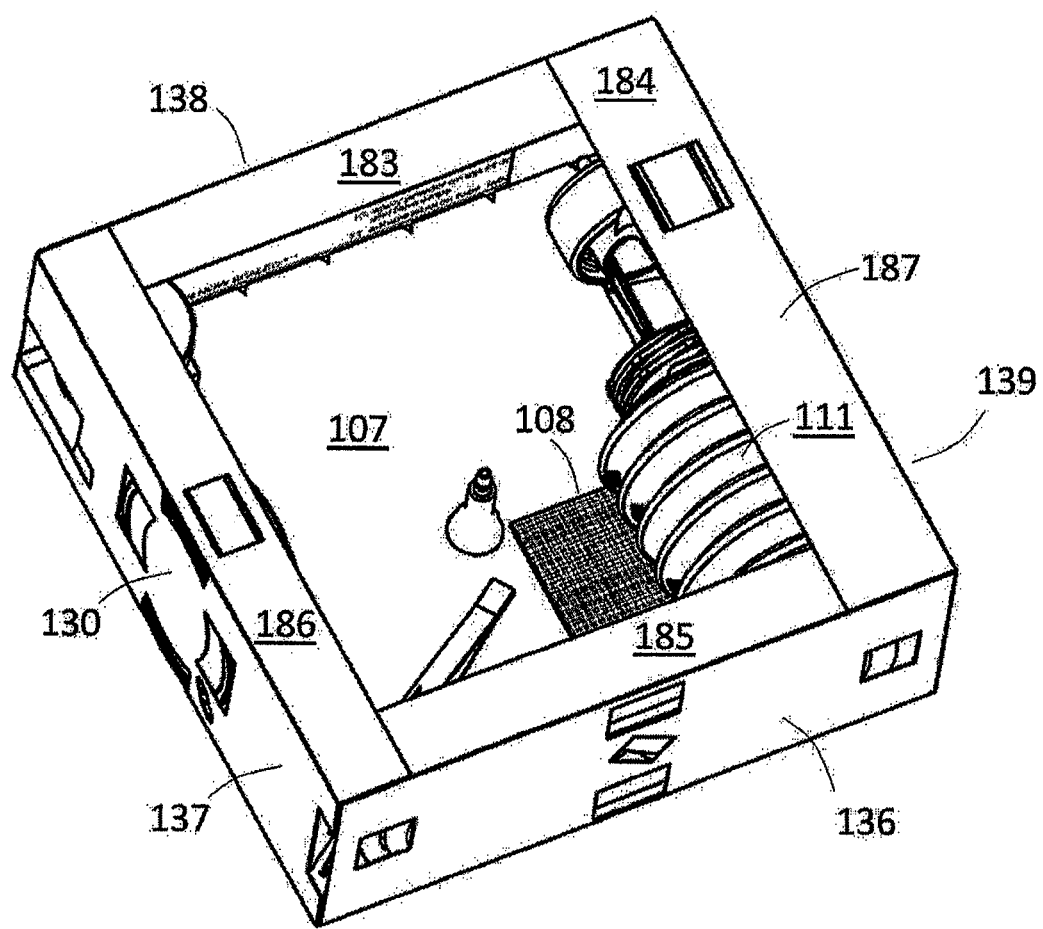

The present invention is particularly beneficial for medical device kits with at least one component that has a large planar profile, but is small along the axis perpendicular to the plane, such as the drape 107 and gauze 108 components. For this type of kit, at least one planar component can be placed on the bottom of the base 135 enclosure, with or without retention features in the mounting card to secure its position, as shown for the drape 107 and gauze 108 components in FIG. 23, and in at least one preferred embodiment, any additional components can rest about any central planar components, while being mounted on the base, sidewalls, and/or other packaging features, as shown for components 101 through 106 and 109 through 115 in FIG. 23. In the preferable embodiment, these additional components are not mounted on the base, unless under the planar components, as this would otherwise increase the footprint of the packaging. At least one component may be left unmounted above the central planar components; however, this is not preferable. At least one component on the sidewalls, including device components and retention structures, may be used to hold at least one central component in-place, when the sidewalls are folded into their final packaging configuration. This is shown in FIG. 24B, where the bellows pump 111 is constraining the drape 107 and gauze 108 onto the base 135 (not labeled and/or visible in FIG. 24B) of the packaging, when the mounting card is folded into its final packaging configuration. In the embodiment shown in FIG. 24B, the gauze 108 protects the drape 107 from any damage that may be caused by the accordion folds of the bellows pump 111.

The disclosed mounting card design eliminates the need for draft (i.e., taper) angles that are otherwise necessary for the manufacture of vertical pockets and/or vertical walls in thermoformed trays. This draft angle requirement may significantly increase the footprint of the package, particularly in the case that deep pockets and/or high walls are necessary. In the present invention, the components are mounted onto the sidewalls, which can be folded to the equivalent of a 0 (zero) degree draft angle from the vertical direction, as shown in FIGS. 24A and 24B. The equivalent of negative draft angles is also possible, in the case that at least one sidewall is folded by more than 90 degrees. Eliminating a draft angle requirement for the walls and/or features in the present invention creates an ideal packaging design for medical devices with at least one component that is long along the vertical axis of its final packaging configuration, such as the bellows pump 111. Even when the vertical axis of its final packaging configuration is chosen to be its axis of minimum length (i.e., the diameter of the pump), the bellows pump 111 requires a deep pocket and/or high walls in many of its corresponding packaging designs, particularly when kitted with other components and/or when using nonflexible packaging options.

The present invention is ideal for medical devices with multiple components, at least one being large in its planar profile, but small in its vertical axis, such as the drape 107 and gauze 108 components, and at least one being large in its axis of minimum length and/or along its vertical axis of its final packaging configuration, such as the bellows pump 111. These components can be mounted on the base of the enclosed volume for the large planar component(s) and on at least one of the sidewalls and/or other packaging features connected to the sidewalls 210 through 213 of FIGS. 17A and 21 for the bulkier components, which can help to minimize the footprint and/or volume of a final, preferably stackable package.

Figure 17A:
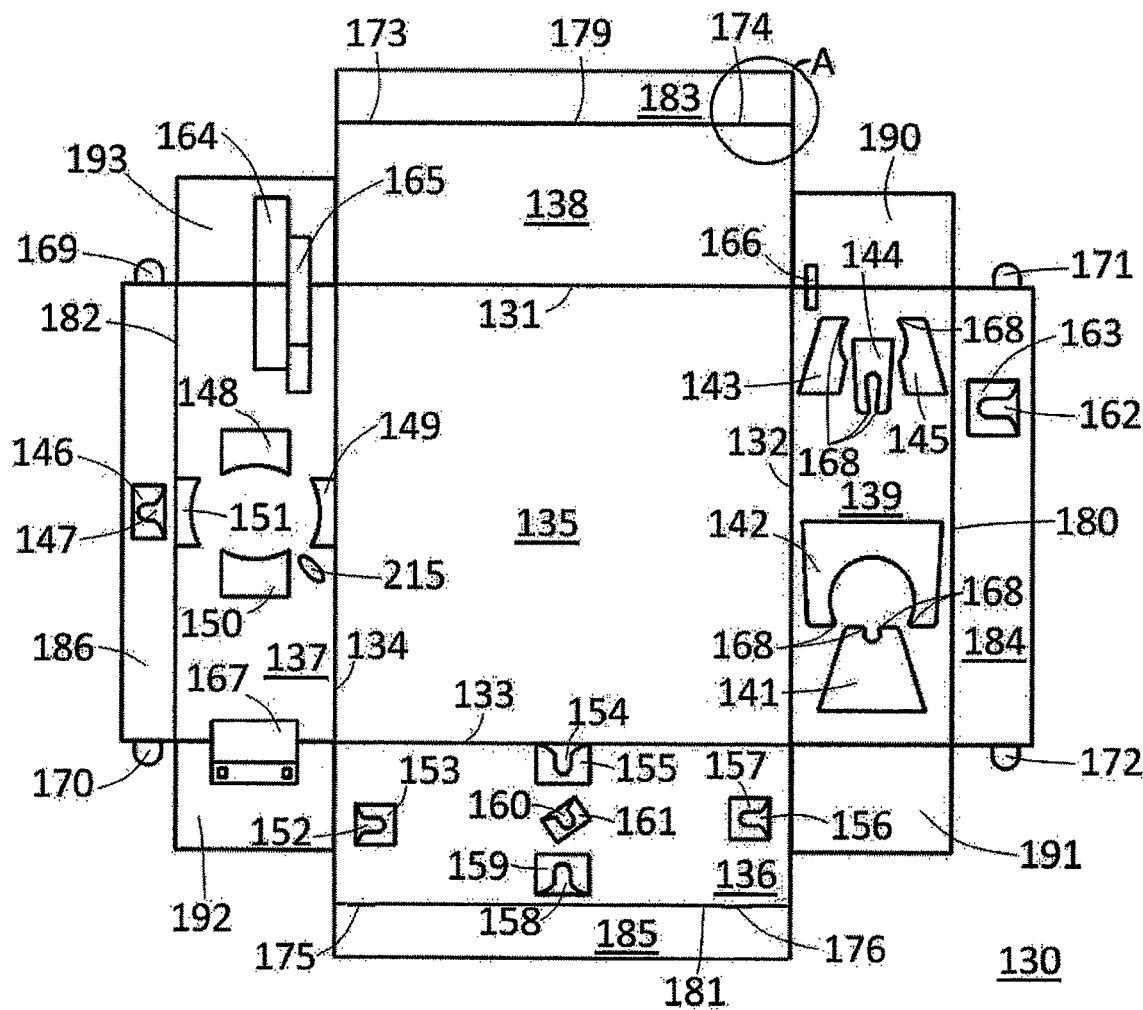
FIG. 17A is a schematic top plane view of a novel mounting card-type packaging according to the present invention.
Figure 17B:
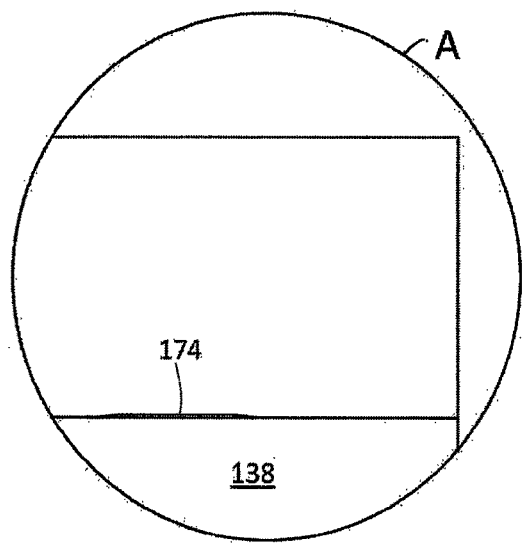
FIG. 17B is an enlarged view of a portion of FIG. 17A.

The sidewalls can be held in place for easy stackability. This can be done in various ways, including by incorporating features (e.g., folding tab features 169 through 172 of FIGS. 17A and 24A and the corresponding slots 173 through 176 of FIGS. 17A, 17B, and 24A for the tab features to lock into) to temporarily interlock and/or hold the sidewalls together at, at least one location along the contact points between two adjacent sidewalls and/or features connected to two adjacent sidewalls, and/or by constraining the side walls with at least one of an exterior wrap (e.g., a central supply room (CSR) wrap 177 of FIGS. 25 and 26), bag 178 of FIGS. 27A and 27B, and/or pouch. Preferably, features in the planar sheet temporarily interlock and/or hold at least one pair of adjacent sidewalls together; more preferably, features temporarily interlock and/or hold at least every other adjacent sidewall together when moving around the base in a clockwise or counterclockwise direction; and more preferably, features temporarily interlock and/or hold every adjacent sidewall together. This produces a more robust structure for withstanding outside forces during shipping, storage, and/or handling, which also enhances the stackability of the final packaging configuration. In other constructions, at least one type of adhesive can be utilized to temporarily attach one or more sidewalls, although one of the advantages of the present invention is the elimination of adhesive during assembly, which saves at least one manufacturing step. Moreover, eliminating adhesive obviates the need to limit shelf life based on expected duration of the adhesive, especially in hot and/or humid conditions.

In some embodiments, at least one folding line 179 through 182 of FIG. 17A on the top of at least one of the sidewalls is used to create at least one lip 183 through 186 of FIGS. 17A and 24B that can fold parallel to the base 135 of the packaging, as shown in FIG. 24B. In at least one preferred embodiment, at least one lip includes at least one feature to interlock and/or hold the corresponding sidewall and at least one of its adjacent sidewalls temporarily in-place (e.g., folding tab features 169 through 172 of FIGS. 17A and 24A and the corresponding slots 173 through 176 of FIGS. 17A, 17B, and 24A for the tab features to lock into). The lip features may also incorporate at least one retention feature to hold at least one component, such as the retention fold pairs 146-147 and 162-163, which hold the cotton swabs 102 and ruler 103 with fold pair 146-147 and the powder stickpack 113 with 162-163, as shown in FIG. 23. These components are preferably held in the enclosed volume 140, such that these components do not extend past the top surface of the final packaging embodiment.

In the case that components are mounted outside the enclosed volume 140, it may be preferable that the retention features and their corresponding device components remain within, or at least close to within, the volume formed by the planes of the sidewalls, top of the final packaging embodiment, and base of the final packaging embodiment, as not to stick out. Therefore, if necessary, components that are thin along at least one axis and can lie flat on the surface(s) they are mounted onto, such that their dimension(s) perpendicular to the mounting surface(s) is small (i.e., thin), are most preferable for mounting outside of the enclosed volume.

The top planar contact surface is defined as the planar surface that has at least three points of contact when placed on top of the final packaging configuration. In order to increase the stackability of the final packaging configuration, the top planar contact surface is relatively parallel to the base with an inclusive angle of preferably −10 degrees to +10 degrees, and more preferably −5 degrees to +5 degrees. In the most preferred embodiment, this plane is parallel to the base by −1 degrees to +1 degrees.

In a preferred embodiment, the sidewalls have folding lines 179 through 182 of FIG. 17A that create lip features 183 through 186 of FIG. 24B, which create a lip around at least a majority of the top perimeter of the enclosed volume when the card is folded into its final packaging configuration, as shown by the perimeter 187 in FIG. 24B, which may increase stackability. In one embodiment, at least every other sidewall contains a lip feature, and in another embodiment, every sidewall contains a lip feature, which is typically more preferable. In the preferred embodiment, the lip features are as wide as 50 to 100 percent of the width of the corresponding sidewall, and in a more preferred embodiment, the lip features are as wide as 75 to 100 percent of the width of the corresponding sidewall, and in the most preferred embodiment, the lip features are as wide as 90 to 100 percent of the width of the corresponding sidewall. Also, in a preferred embodiment, features on the lips temporarily interlock and/or hold themselves to their adjacent sidewalls, adjacent lips, and/or other features connected to the adjacent sidewalls (e.g., folding tab features 169 through 172 of FIGS. 17A and 24A and the corresponding slots 173 through 176 of FIGS. 17A, 17B, and 24A for the tab features to lock into). These features may further improve the robustness and stackability of the final packaging configuration.

Figure 28:
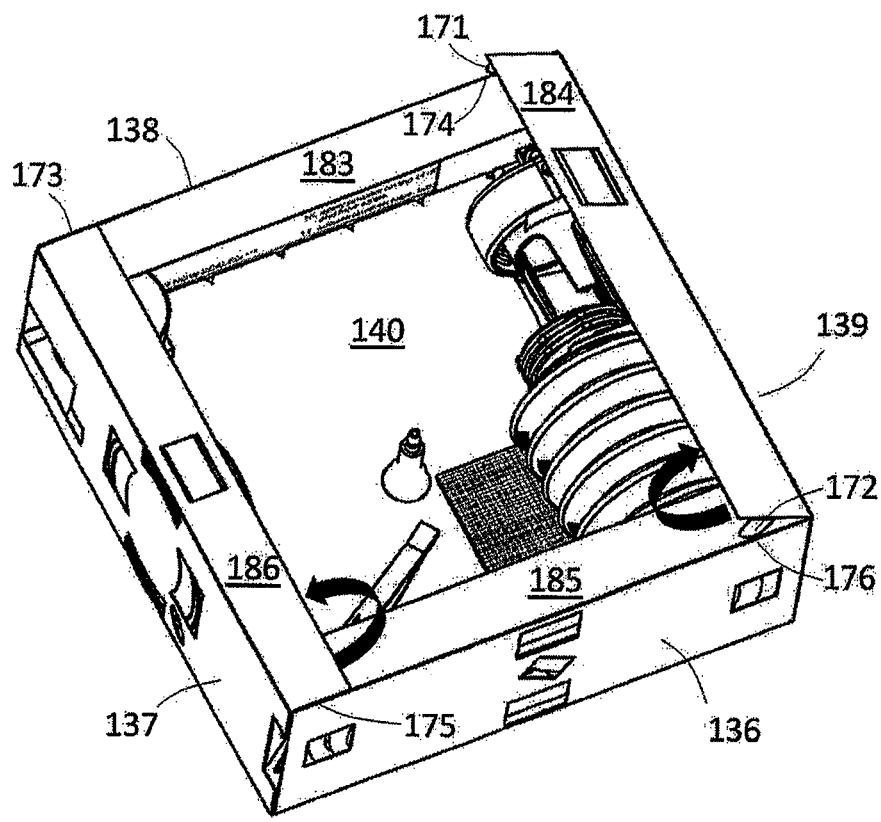
FIGS. 28-29 are schematic perspective views showing unwrapping and deployment of the package of FIGS. 24A-27B.

In one embodiment, the final packaging configuration has an even number of sidewalls 136 through 139 and each sidewall has at least one lip feature 183 through 186, as shown in FIG. 24B. Every other opposing lip group (i.e., lip groups include 183-185 and 184-186) when moving around the base in a clockwise or counterclockwise direction has folding tabs 169 through 172 on both sides of both lips 184 and 186 in the group. These tabs can fold 90 degrees into the enclosed volume 140 of the final packaging configuration, as shown with tabs 171 and 172 in FIG. 24A. In their folded configuration, these tabs can be slid into slots 173 through 176 of FIGS. 17A, 17B, and 24A on the folding line of their adjacent lips in the final packaging configuration, which can temporarily interlock them into place, as shown in FIGS. 24A and 24B. This can create a stable, stackable packaging design for shipping, storage, and/or handling. With this design, when a user wants to use the device, they simply lift the lips 184 and 186 with the tabs 169, 170, 171, and 172 in order to remove them from their corresponding slots 173, 175, 174, and 176, respectively, as shown in FIG. 28. Then, with the proper gauge of the mounting card material, design of the sidewall folding lines, and weight of the components on the sidewalls, at least one of sidewalls may fall due to gravity into the plane of the working surface (e.g., table, cart, and floor), as shown for sidewalls 136, 137, and 139 in FIG. 29. Otherwise the card can be manually manipulated to the desired positioning. This creates a design method that presents all of the components to the user with easy access, while capable of utilizing all of the available packaging real estate (by area and/or volume) and/or maintaining the smallest footprint. A person skilled in the art, after reviewing the present disclosure, would realize that these folding tab and slot features can be integrated into the sidewall edges, as well as into other features connected to the sidewalls.

In the previous folding tab embodiment, it is preferred that the material selection and feature design will allow the tabs to remain in their corresponding slots until the user removes them. However, this design relies on many factors, including geometric tolerances, particularly of the tabs and slots, friction between the surfaces contacting the tabs, weight of the components mounted on the lips and/or sidewalls, orientation of the packaging, and stiffness of the folding lines of the sidewalls, lips, and tabs. Additional packaging components, such as at least one of an exterior wrap (e.g., a central supply room (CSR) wrap 177 of FIGS. 25 and 26), bag 178 of FIGS. 27A and 27B, and/or pouch, can be added to hold the tab features in their corresponding slots and/or the lips parallel to the base, as shown in FIGS. 25 through 27B; this can also be accomplished by applying a weight to the top of the lips with tab features, in order to hold them in-place. In addition, different interlocking and/or holding features than folding tabs 169 through 172 may be used that may be more secure in their final packaging configuration.

Figure 30:
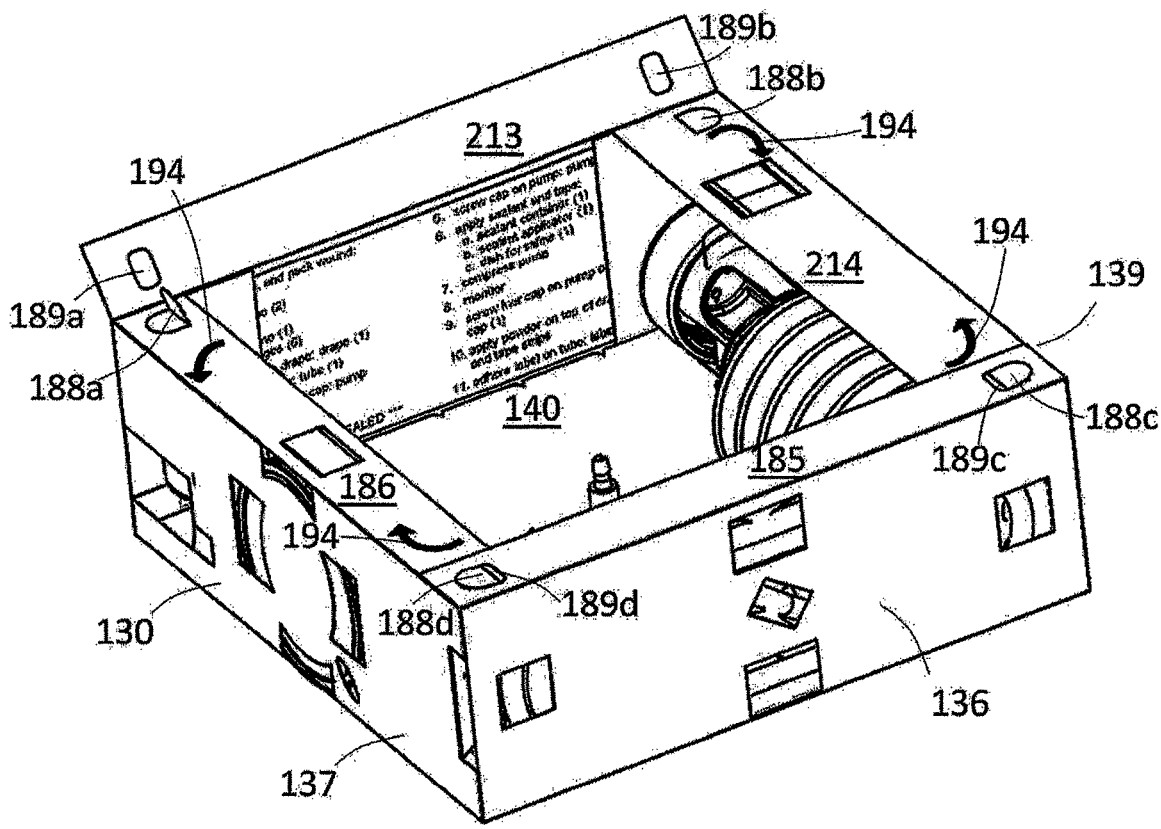
FIG. 30 is a schematic perspective view illustrating interlocking tabs and holes utilized according to the present invention.

Another design may incorporate interlocking tabs 188 of FIG. 30 or similar features cut out of every other group of two opposing lips, sidewalls, and/or features connected to the sidewalls, preferably at a distance inward from their edges. These features may in turn correspond to holes 189 FIG. 30 in their adjacent, contacting lips, sidewalls, and/or features connected to the sidewalls. Preferably, the size and shape of the holes 189 and their corresponding interlocking tabs 188 provide the necessary constraints, such that the side walls cannot fold outward without first manually removing the tabs from the holes. In order to achieve these constraints, the edge of the hole preferably contacts an edge of the tab and/or the tab folding line (or other contact surface) under the tab that opposes the unfolding of the two corresponding sidewalls (i.e., the sidewalls with the interlocking tab and its corresponding hole). One preferred orientation of the tab 188 is a tab that points in the direction of the unfolding of its corresponding sidewall, as shown in FIG. 30; another preferred orientation is a tab that points opposite (i.e., 180 degrees) the direction of the unfolding of the sidewall that corresponds with its corresponding hole. Any tab pointing in the 90 degree span between these two orientations may be preferable. In one embodiment, the preferred orientation is at an angle of 45 degrees (or in the center of the span of 90 degrees). In general, any orientation may be designed to function, and various orientations may serve different constraint purposes. In FIG. 30, one possible orientation of the tabs 188 and holes 189 are shown on the lips 183 through 186 of a packaging design, in various positions: tab 188a is at the assembly position for insertion into the corresponding hole 189a; tab 188b is in its flat, stamped, manufactured position; and tabs 188c and 188d are shown in their assembled positions, locked into holes 189c and 189d, respectively.

A person skilled in the art would realize that various configurations of holes 189 and interlocking tabs 188 can be used to achieve the necessary constraints. Multiple tabs and holes, which may vary in size and rotation angle, may be incorporated into the design at the location where two lips, sidewalls, features connected to the sidewalls, and/or any combination between them overlap; this may increase the number of constraints, increase the constraint options, increase the robustness of the design, and/or decrease the necessary tolerance between each tab and its corresponding hole. With decreased tolerances, the tabs may be easier to insert and/or remove from each corresponding hole. In addition, the lip, sidewall, and/or feature connected to the sidewall that contains tabs and corresponding holes can also vary, and one lip, sidewall, and/or feature connected to the sidewall can contain at least one hole, at least one tab, or at least one hole and tab. Features other than interlocking tabs and corresponding holes are also possible to interlock the adjacent and/or contacting lips and/or sidewalls together, and may be used in combination with interlocking tabs and corresponding holes; this includes folding tabs and corresponding slots. In addition, multiple interlocking tabs can insert into one hole; this may increase the number of constraints, increase the robustness of the design, and/or decrease the necessary tolerance.

These tabs can be folded into their corresponding holes in order to interlock the lips together, as shown in FIG. 30 tabs 188c and 188d and corresponding holes 189c and 189d. When the lip with the tab is under the lip with the corresponding hole, as shown in FIG. 30, the tab is folded up through the corresponding hole, and overlap of the tab onto the top of the adjacent lip locks the lips together, as shown in FIG. 30. In a preferable embodiment, the stiffness of the folding line of the tab forces the tab to lie substantially parallel to the bottom of the packaging system in its final configuration, such that no tabs substantially stick out from the top of the packaging plane, as shown in FIG. 30 tabs 188c and 188d and corresponding holes 189c and 189d; this is similar to the retention folds in the case that no components, or substantially thin components, are being retained. Then, when a user wants to use the device, they may have to simply lift the lips with the holes in the preferable embodiment, as shown by the configuration of lip 183 in FIG. 30, causing the tabs to be removed from their corresponding holes, and/or they may have to lift the tabs and push them through the holes, and/or they may have to push the lips with the tabs downward to remove the tabs from the holes. The method(s) that can be used depends on factors including the stiffness of the folding lines, orientation of the tabs, and constraint geometries of the holes. Also, depending on the design, the third option may not be easily performed, due to interference of medical device components and/or their mounting card holding mechanisms. Then, with the proper gauge of the mounting card material, design of the sidewall folds, and weight of the components on the sidewalls, at least one of sidewalls may fall due to gravity into the plane of the working surface (e.g., table, cart, and floor), as shown for sidewalls 136, 137, and 139 in FIG. 29. This will happen with the proper gauge of the mounting card material, design of the sidewall folds, and weight of the components on the sidewalls. Otherwise the card can be manually manipulated to the desired positioning.

When the lip with the tab is on top of the lip with the corresponding hole, the tab is folded down through the corresponding hole, and overlap of the tab onto the bottom of the adjacent lip locks the lips together. The stiffness of the folding line of the tab allows the tab to interlock into the corresponding hole, in order to achieve the proper constraints; this is similar to the retention folds in the case that no components, or substantially thin components, are being retained. This orientation avoids any potential unnecessary protrusions of the tabs upward from the top plane of the final packaging orientation. However, it also requires that the tabs enter into the internal volume 140 of the final configuration of the packaging, which may not be ideal if medical device components and/or their mounting card holding mechanisms interfere with the tabs and/or block their access during assembly. When a user wants to use the device, they may have to simply lift the lips with the tabs, causing the tabs to be removed from their corresponding holes in the preferable embodiment, they may have to lift the tabs and push them through the holes, and/or they may have to push the lips with the holes downward to remove the tabs from the holes. The method(s) that can be used depends on factors including the stiffness of the folding lines, orientation of the tabs, and constraint geometries of the holes. Depending on the design, the second and third options may not be easily performed, due to interference (visually and/or physically) of medical device components and/or their mounting card holding mechanisms. After the lips, sidewalls, and/or features connected to the sidewalls are disengaged from each other, at least one of the sidewalls may fall due to gravity into the plane of the working surface (e.g., table, cart, and floor), as shown for sidewalls 136, 137, and 139 in FIG. 29. This will happen with the proper gauge of the mounting card material, design of the sidewall folds, and weight of the components on the sidewalls. Otherwise the card can be manually manipulated to the desired positioning.

In certain circumstances, at least one tab or other feature that constrains at least one sidewall from folding inward (i.e., into the enclosed volume 140) may be desirable. This may be the case if stackability is a concern, and heavy weight may be placed onto the package, and/or the sidewall folding lines 131 through 134 are highly flexible. In order to achieve this constraint, one preferred orientation of the tab 188 is a tab that points opposite (i.e., 180 degrees) the direction of the unfolding of its corresponding sidewall (in the example embodiment in FIG. 30, this is preferable if the lip with the tab is under the lip with the hole); another preferred orientation is a tab that points in the direction of the unfolding of the sidewall that corresponds with its corresponding hole (in the example embodiment in FIG. 30, this is preferable if the lip with the hole is under the lip with the tab). Any tab pointing in the 90 degree span between these two orientations may be preferable. In one embodiment, the preferred orientation is at an angle of 45 degrees (or in the center of the span of 90 degrees). However, typically, there is one tab angle that satisfies all necessary constraints, based on the design of the entire packaging embodiment. For example, for the packaging embodiment shown in FIG. 30, the sidewalls would be constrained in both the folding and unfolding directions if the tabs were each rotated 45 degrees towards the center of their corresponding lip, as shown by the arrows 194.

In some embodiments, instead of using interlocking and/or holding tabs in multiple directions in order to provide and/or improve the load bearing properties of the packaging design, a tapered wall design may be used as a novel embodiment of the current invention. In this embodiment, the walls are tapered at an angle either outward or inward from the enclosed volume 140. For the outward angled sidewalls, the angle is preferably between 5 to 60 degrees and more preferably between 10 to 45 degrees. In the preferred embodiment, all of the sidewalls are interlocked to the adjacent sidewall, such that the edge of their sidewalls are held together preferably at the top of their length, more preferably at least along the top third of their length in an intermittent or continuous fashion, and more preferably throughout a majority of their length in an intermittent or continuous fashion. The necessary level of constraint depends on factors, including gauge and material of the mounting card material, design of the sidewall folds, and weight of the components on the sidewalls. The orientation direction of the interlocking mechanism can constrain the sidewalls in the circumferential/outward direction, such that the taper angle will not get larger. Then, as the packaging bears a vertical load, the load will try to force the angle to get larger; however, the interlocking mechanisms will bear increased tensile load, while tightening the interlocking mechanisms and forming a more stable structure.

For the inward angled sidewalls, the angle is preferably between 5 to 60 degrees and more preferably between 10 to 45 degrees. In the preferred embodiment, all of the sidewalls are interlocked to the adjacent sidewall, such that the edge of their sidewalls are held together preferably at the bottom of their length, more preferably at least along the bottom third of their length in an intermittent or continuous fashion, and more preferably throughout a majority of their length in an intermittent or continuous fashion. The necessary level of constraint depends on factors, including gauge and material of the mounting card material, design of the sidewall folds, and weight of the components on the sidewalls. The orientation direction of the interlocking mechanism can constrain the sidewalls, such that the taper angle will not get larger. Then, as the packaging bears a vertical load, ideally the sidewalls will apply more weight to each other, bearing an increased compressive force and more stable structure. These may be more stable designs than walls approaching 90 degrees, as when the walls are loaded, they may buckle; the structure does not inherently increase in stability with increasing load, instead it decreases in stability in most cases.

One technique to minimize buckling, including designs with no taper, is to include off-plane features attached to the side walls, such as sidewall folds 190-193 that are folded perpendicular to the sidewalls, giving their corresponding sidewall increased structural stability.

A person skilled in the art would realize that the same features described above can be used in packaging configurations with an odd number of sidewalls. However, in this case, there will not be an even number of opposing lip, sidewall, and/or feature connected to the sidewall groups. Therefore (for example), if each sidewall incorporates a lip that overlaps with the lip of both adjacent sidewalls, then the minimum number of folding stages of lips is three, instead of two folding stages for packaging with an even number of sidewalls, where every other opposing lip group can be folded at once (i.e., a folding stage). With this, the embodiments described above where every lip has the same interlocking and/or holding features on each side is not possible. If an odd number of sidewalls exist, then at least one lip must have at least one different interlocking and/or holding feature on each side. In addition, one skilled in the art would realize that if at least one lip of a packaging design with an even number of sidewalls had at least one different interlocking and/or holding feature on each side, then this must be the case for at least one more lip. This argument also extends to other features such as sidewall and/or feature connected to the sidewalls.

Figure 29:
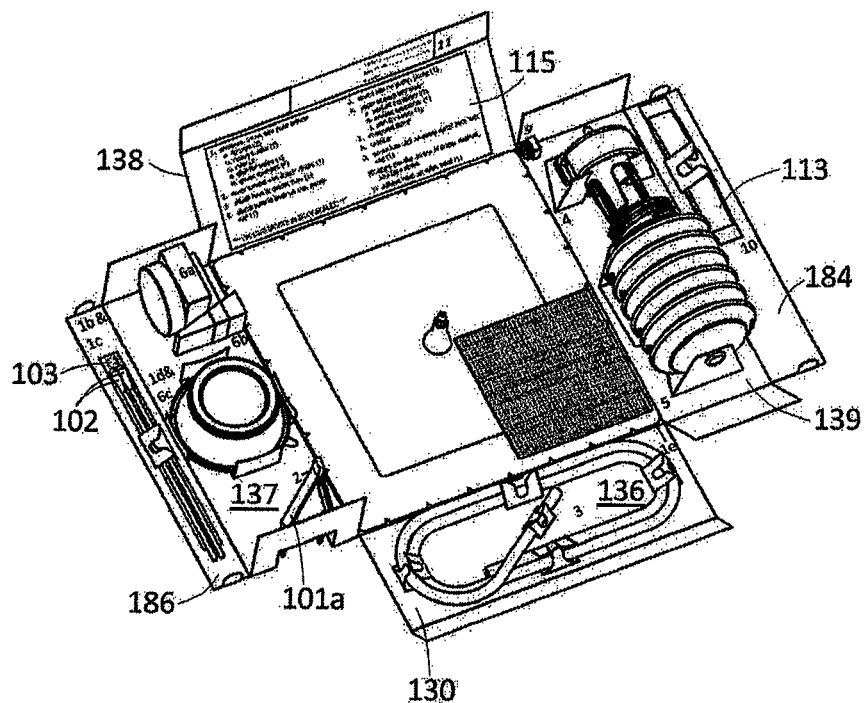

The gauge of the mounting card material, design of the sidewall folds (i.e., folding lines) 131 through 134, and weight of the components on the sidewalls can all be manipulated such that the sidewall does not fall flat, if desirable. In one embodiment, the sidewall furthest from the user 138 of FIGS. 17A and 29, may contain printed instructions 115 of FIGS. 16 and 29 on the surface facing the user. (These can be printed directly onto the mounting card or attached to the mounting card, such as with an adhesive label shown in FIGS. 16 and 29.) Therefore, it may be desirable for the sidewall to remain folded between 0 and 90 degrees upon the disengagement of the corresponding sidewall and/or lip from any other sidewall and/or lip, in order for the user to easily read the instructions while using the device; this configuration is shown in FIG. 29. In one preferred embodiment, the desired angle of the fold is between 20 and 80 degrees, and in another preferred embodiment, it is between 30 and 60 degrees. The user may also manually manipulate the sidewall to the desired angle.

Figure 16:
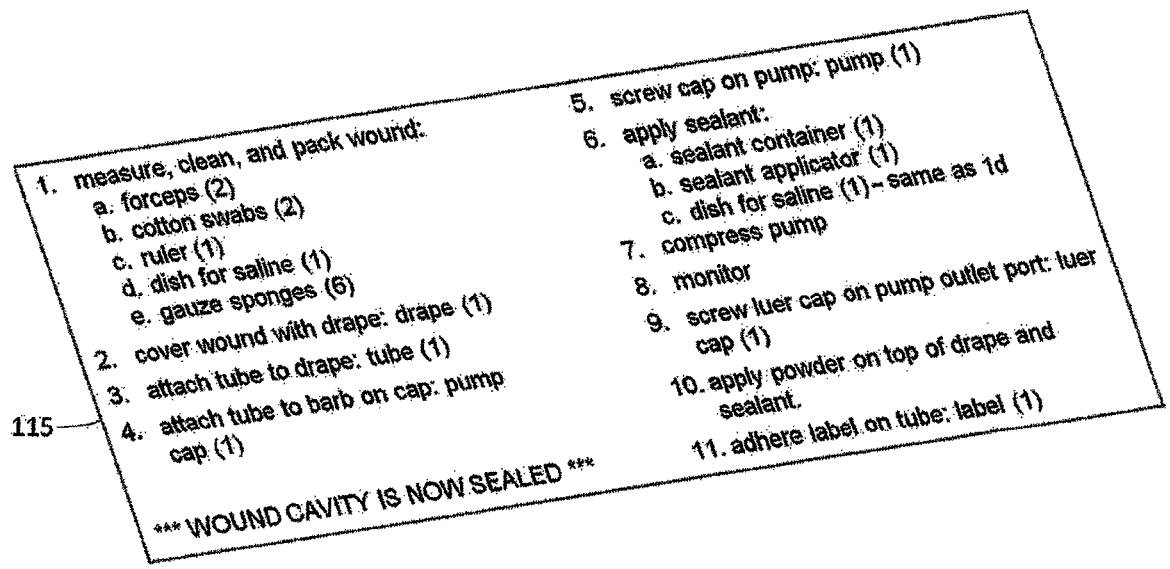
FIG. 16 is a schematic perspective view of an instruction label.
Figure 17C:
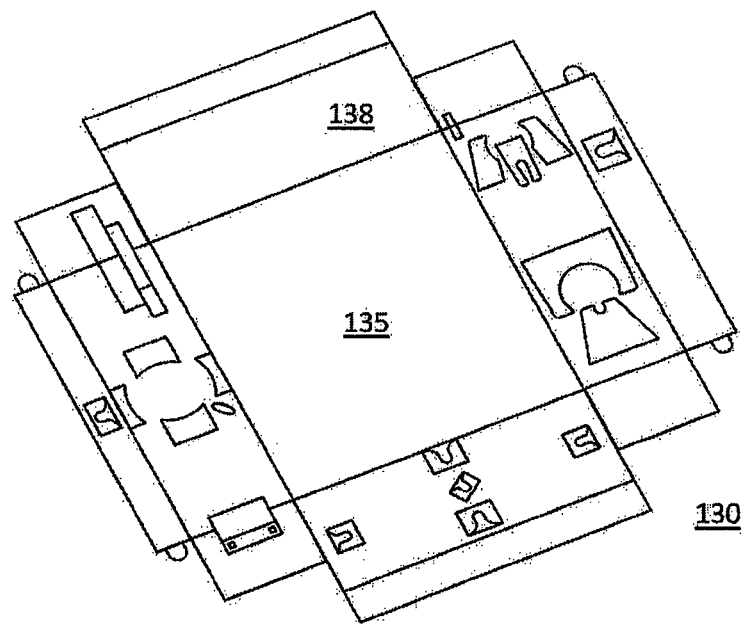
FIG. 17C is a schematic perspective view of the mounting card of FIG. 17A.
Figure 17D:
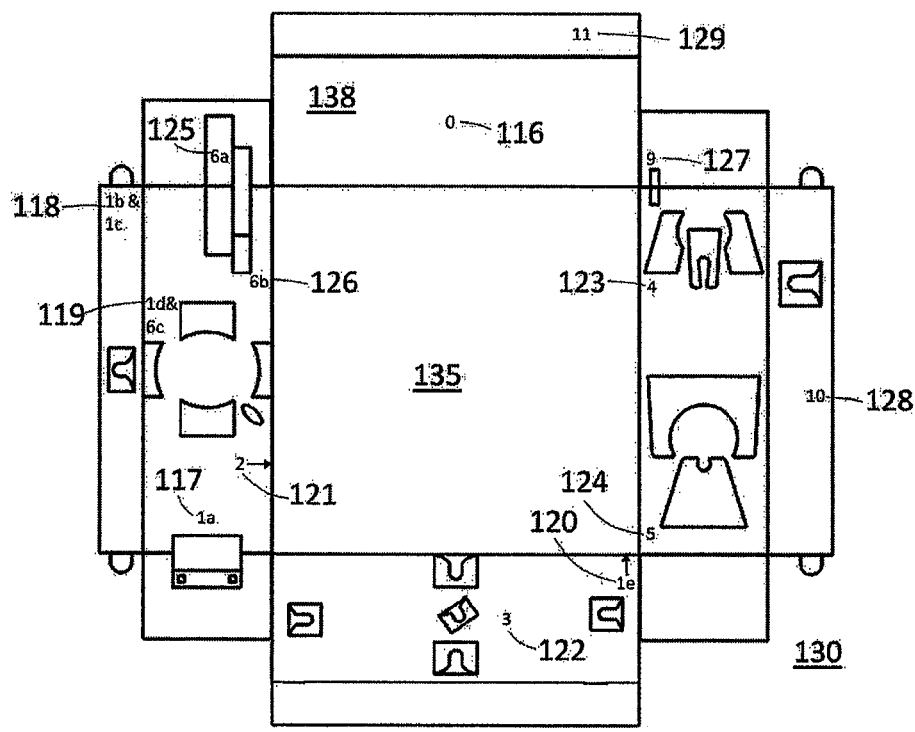
FIG. 17D is a schematic top plane view of the novel mounting card-type packaging of FIG. 17A with printed component (reference number) labeling.
Figure 18C:
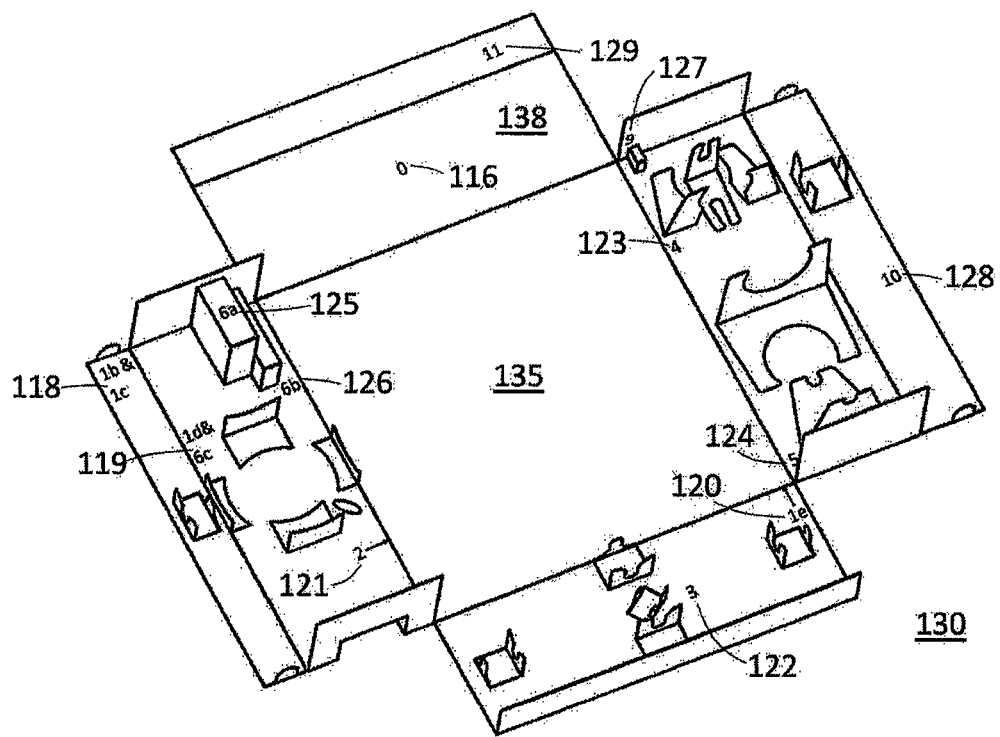
FIG. 18C is a schematic perspective view of the mounting card of FIG. 17D with mounting features raised.

The instructions on the sidewall may be step-by-step instructions 115 that have labels, such as numbers as shown in FIG. 16, that correspond to labels of the components on the card, as shown in FIG. 17D (without components) and 23 (with components), and/or on the components themselves. These labels can be printed directly onto the mounting card and/or components or attached to the mounting card and/or components, such as with an adhesive label. (Note that the numerical label zero ("0") in the FIGS. 17D, 18C, and 20 does not need to be printed, as it is covered by the numerical instructions 147 in the final packaging embodiment, which reference the other component numbers; in addition, the instructions may be printed directly onto the card, in which case that the numerical label zero ("0") should not be printed.)

The folds for the lips have similar properties to the folds for the sidewalls, and therefore, can also be made to fall flat or maintain an angle. In order for a fold to fall flat after opening, a thinner gauge material can be used for the mounting card, features such as perforations or score lines can be added to a folding line, in order to weaken it, and/or heavy components can be mounted to the corresponding lip, as shown in FIG. 29 for lips 184 and 186 which have fallen to a flat position. Score lines can be made on either side of the mounting card, as perforations typically are through the thickness of the mounting card.

The desired gauge of the mounting card is influenced by many factors, including the material of the mounting card, weight of the medical device components to be mounted, design of the component holding functional features cut into the card (e.g., retention tabs, folds, and/or straps), and desired robustness and stackability of the final configuration. A desirable thickness may be preferably between 0 mil and 100 mil, more preferably between 4 mil and 50 mil, even more preferably between 8 mil and 40 mil, and most preferably between 15 mil and 35 mil. Typically, an increase in the number of folds and/or interlocking mechanisms in the design leads to a decrease in the necessary thickness of the material, since the structural robustness is often increased. This is also the case when additional constraints are applied to the exterior of the mounting card, such as an exterior wrap (e.g., a central supply room (CSR) wrap 177 of FIGS. 25 and 26), bag 178 of FIGS. 27A and 27B, and/or pouch.

Figure 19:
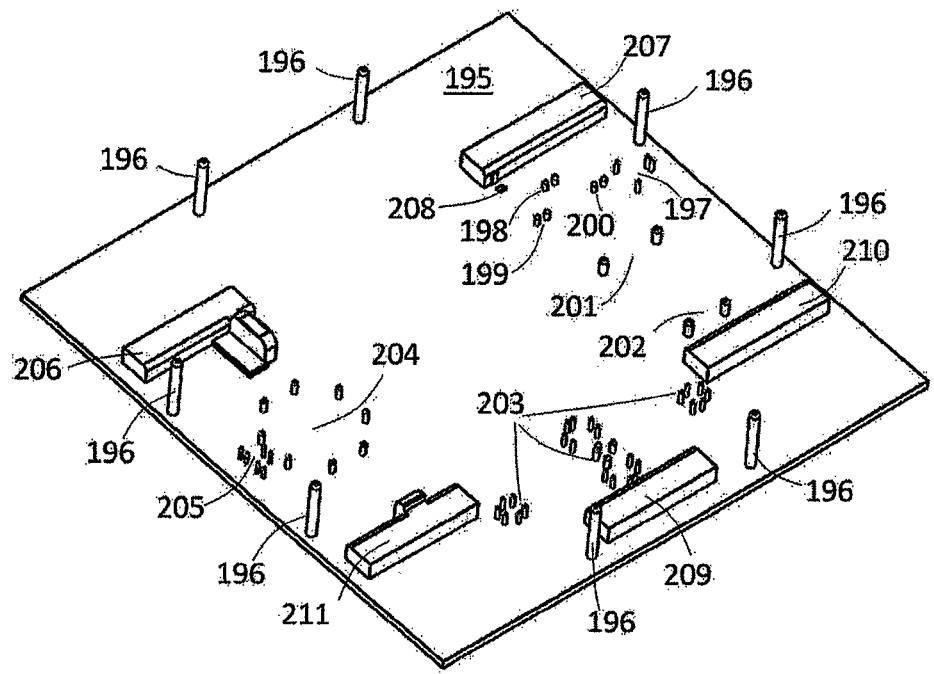
FIG. 19 is a schematic perspective view of a jig according to the present invention.
Figure 20:
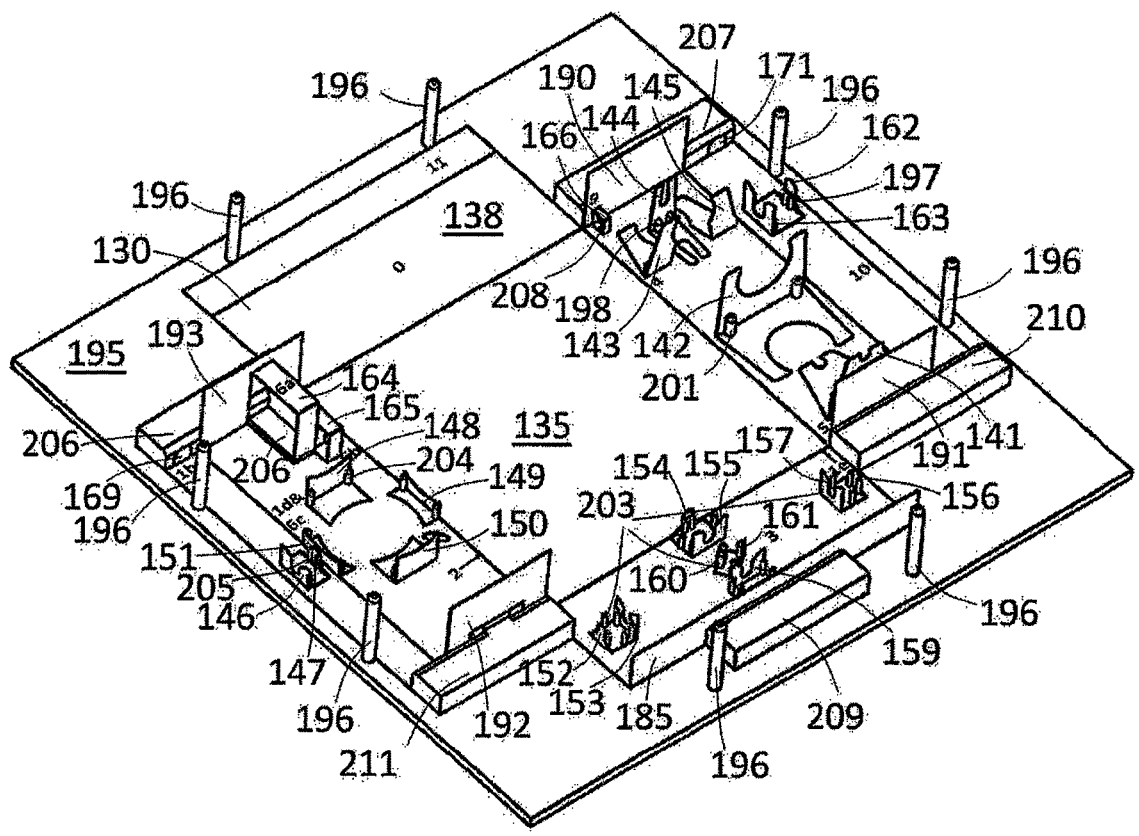
FIG. 20 is a schematic perspective view of the mounting card of FIG. 18C secured on the jig of FIG. 19.

Mounting cards may be assembled by-hand; however, folding and loading a mounting card may be a tedious process, which may lead to long assembly times. To overcome this, the present patent application discloses a method of loading that includes at least one jig 195 of FIG. 19. When the card 130 is pressed onto a jig 195, at least one feature on the jig may manipulate at least one feature on the card. As shown in FIGS. 19 and 20, pins 196 are alignment/locating pins to help align the edges of the mounting card for proper jig loading; alternatively or simultaneously, at least one locating pin and/or other feature can be used that may insert into, or otherwise integrate with, at least one feature cut into the mounting card. As shown in the FIGS. 19 and 20, features on the jig 195 manipulate features on the mounting card 130 into their loading positions: pin group 197 positions retention folds 162 and 163 perpendicular to the jig; pin group 198 positions retention tab 144 perpendicular to the jig; pin group 199 (not visible in FIG. 21) positions retention tab 143 perpendicular to the jig; pin group 200 (not visible in FIG. 21) positions retention tab 145 perpendicular to the jig; pin group 201 positions retention tab 142 perpendicular to the jig; pin group 202 (not visible in FIG. 21) positions retention tab 141 perpendicular to the jig; pin group 203 positions retention folds 152 through 161 perpendicular to the jig (158 is not visible in FIG. 21); pin group 204 positions retention folds 148 through 151 perpendicular to the jig; pin group 205 positions retention folds 146 and 147 perpendicular to the jig; protrusion 206 folds tab 169 perpendicular to the jig (i.e., its assembly position) and folds sidewall fold 193 perpendicular to the jig which, along with the features of 206, aids the pop-up of retention straps 164 and 165 to their loading positions; protrusion 207 folds tab 171 perpendicular to the jig (i.e., its assembly position) and folds sidewall fold 190 perpendicular to the jig which, along with the help of angled protrusion 208, aids the pop-up of retention strap 166; protrusion 209 positions lip 185 perpendicular to the jig (i.e., its assembly position); protrusion 210 folds tab 172 (not visible in FIG. 20) perpendicular to the jig (i.e., its assembly position) and folds sidewall fold 191 perpendicular to the jig; and protrusion 211 folds tab 170 (not visible in FIG. 20) perpendicular to the jig (i.e., its assembly position) and folds sidewall fold 192 perpendicular to the jig which, along with the features of 211, aids the pop-up of custom retention feature 167 (not visible in FIG. 20) to its loading position.

As shown in FIG. 20, at least one retention feature (e.g., retention features 162 and 142 are folded to be perpendicular to the base 135, which is their loading position, and retention strap 164 is in the position to receive its corresponding component) may be moved to a position, in order to accept its corresponding component(s), at least one lip and/or at least one of its corresponding interlocking and/or holding features (e.g., a folding tab 171 is folded to be perpendicular to the base 135) may be folded to a desired angle, typically the angle used for assembly or, if different, the angle used for the final packaging, and/or at least one sidewall may be folded to a desired angle, typically the angle used for assembly or, if different, the angle used for the final packaging (not shown in the figures).

In the case that at least one retention feature is prepared to accept its corresponding component(s), the component(s) may then be dropped into at least one feature on the jig, such as recessed areas and/or between pins, that either assist in locking component(s) in their corresponding retention tab(s) and/or hold the component(s) under or between their corresponding retention fold(s). The components may also be directly locked into retention tab features in the card without further assistance from a feature on the jig. As shown in FIG. 21, the powder stickpack 113 is dropped between pins 197 and retention folds 162 and 163; luer lock cap 112 is placed in retention strap 166; bellows pump 111 is placed in retention tabs 141 and 142; pump cap 110 is placed in retention tabs 143, 144 (not visible in FIG. 20), and 145; drainage tube 109 is dropped between pins 203 and retention folds 152 through 161; sealant applicator 106 is placed in retention strap 165; sealant container 105 is placed in retention strap 164; saline container 104 is placed between pins 204 and retention folds 148 through 151; ruler 103 and cotton swabs 102 are placed between pins 205 and retention folds 146 and 147; and forceps 101a is placed into custom retention feature 167.

When the card is lifted from the feature(s) on the jig, any manipulated retention fold(s) preferably fold onto their corresponding component(s), providing the necessary retention force to keep the component in-place, and component(s) preferably remain locked into any manipulated corresponding retention tabs. This is shown in FIG. 23 for when the assembly on the jig in FIG. 21 is lifted off of the jig. Any folds in the lips, interlocking and/or holding features, and/or sidewalls preferably remain in the mounting card. Due to potential shape memory of the design of these folds, they may be folded to a larger angle than desired when the mounting card is manipulated by the jig, in order to account for any reduction in angle upon removal. Additional manipulations of at least one card feature may be manipulated sequentially using the same jig, manipulated using a separate jig, and/or by-hand. When the same jig is used to further manipulate a mounting care, this may be accomplished: with at least one additional jig component that is added to the jig, such as extra pin features placed in corresponding holes; by removing at least one jig component; by manipulating at least one movable jig component, such as a mechanism to fold at least one sidewall and/or manipulate at least one pair of the interlocking and/or holding features on the lips to their final position.

By using at least one jig for loading, the loading of the mounting card is similar to the loading of a tray, where components are dropped and/or snapped into place. In some cases, more complex folds can be made by mechanisms other than jigs, including by-hand or with automation, and may be used in combination with the jigs. In addition, jigs can be loaded, manipulated, and/or unloaded by-hand and/or by automation equipment. Preferably, for high volume medical devices, the majority of the assembly process is automated, and more preferably the entire assembly process is automated.

The present patent discloses a novel kit for mechanical negative pressure wound therapy (NPWT), which is an extension of the technology disclosed in U.S. Pat. No. 9,173,777 B2. The NPWT example presented in this disclosure is a novel negative pressure wound therapy kit, which includes additional components to clean and assess the wound: forceps 101; cotton swabs 102; ruler 103; saline container 104; and additional gauze sponges for cleaning 108. (Instead of a separate component in the kit, the ruler may be printed on at least one component of the final packaging embodiment; in this case, the ruler design may include perforations, scoring, and/or similar features, such that it can be easily torn from the packaging component during its use.) A key feature in using the disclosed packaging design for the NPWT kit for treating wounds is that the packaging design offers an embodiment that can be easily designed into an organized, no-touch wound dressing kit, which may be preferable. Many care facilities require that the staff use a no-touch technique when dressing open wounds, in order to reduce wound infection risk. For a no-touch dressing, the caregiver creates a sterile field with all of the necessary, sterile wound dressing components. Then, the caregiver does not touch the sterile field or any of its components by-hand. Instead, they wear non-sterile gloves and use two sterile forceps 101 and/or tweezers (i.e., one tool in each hand) to manipulate anything in the sterile field and/or any sterile components.

The forceps are only used to manipulate sterile objects and/or touch sterile surfaces. Care must be taken when transferring objects such as gauze from the sterile field to the patient, in order to perform a treatment procedure, such as cleaning the wound. In this case the forceps may be used to handle the components when treating the wound, but they are only allowed to contact the surfaces of the components that remain sterile and have not touched the patient or other non-sterile surface. During the entire procedure, the caregiver typically wears non-sterile gloves.

Figure 25:
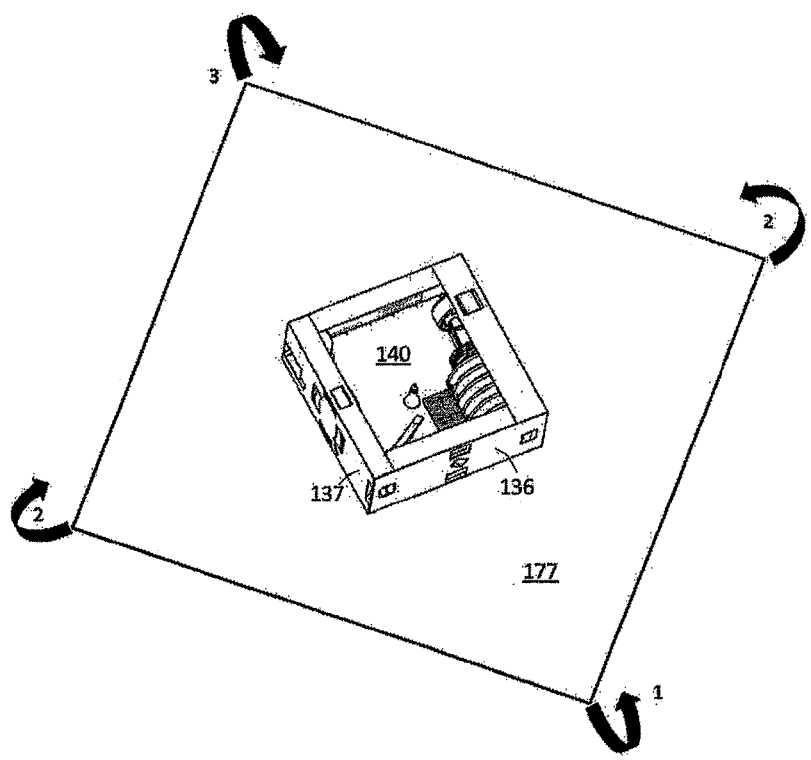
FIGS. 25-27B are schematic perspective views showing wrapping of the package of FIG. 24B, with top and bottom of a final, packaged NPWT kit shown in FIGS. 27A and 27B, respectively.
Figure 26:
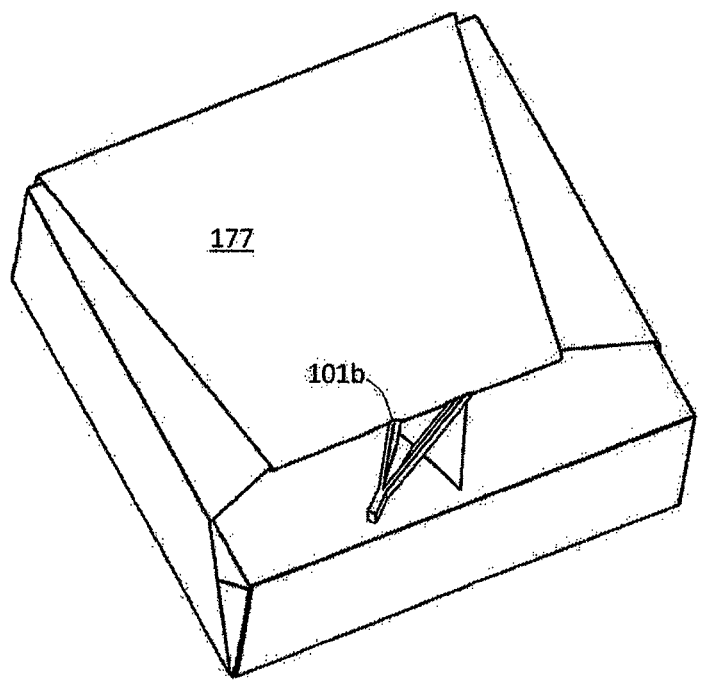
Figure 27A:
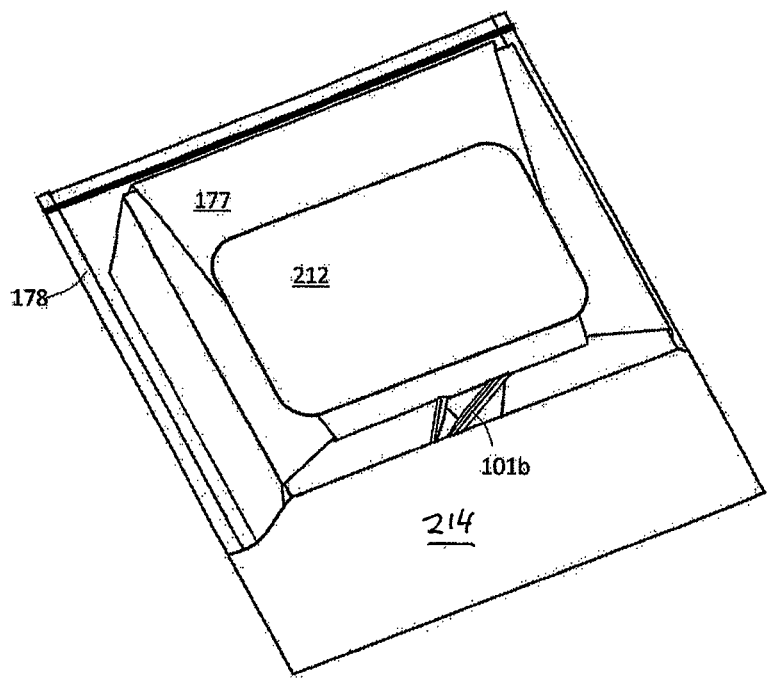
Figure 27B:
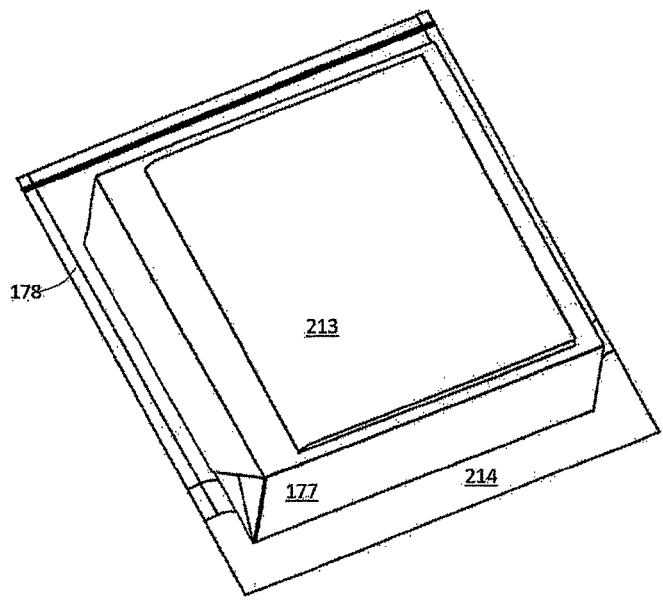

An example of the top and bottom of the final, packaged NPWT kit is shown in FIGS. 27A and 27B, respectively. In general, the final sub-kit is the loaded, final mounting card packaging configuration, as shown in FIG. 24B, which is then wrapped in a CSR wrap 177, as shown in FIGS. 25 and 26. A first forceps 101b in FIGS. 26 and 27A is then tucked into the fold of the CSR wrap 177, such that it is only touching the exterior surface of the CSR wrap 177. This CSR wrap and forceps configuration is commonly used in no-touch wound and surgical kits. The embodiment shown in FIG. 26 is then sealed in a flexible sterile barrier, for which a heat-sealed header bag 178 of FIGS. 27A and 27B is used in the present example. By using a header bag 178, one side of the bag can include an outer label 212 of FIG. 27A, including product information and/or other regulatory required information, and the opposite side can display the IFU (instructions for use) 213 of FIG. 27B. This allows for product information on the displayed cover of the IFU to be presented and read through the clear polymer bag, prior to the opening of the bag, which may assist the caregiver in assuring that the device is the device that was prescribed and/or is applicable for the treatment of the patient. The clear polymer film typically makes up the entire surface of the header bag, except for the area of the header 214 of FIG. 27A. The header may provide venting and/or other properties for the sterilization process, and therefore, it may be preferable to avoid covering it with any labels. In a preferred embodiment EtO sterilization is used.

The side of the header bag 178 with the outer label 212 and IFU 213 may be reversed, or the outer label 212 and IFU 213 may be placed on the same side of the header bag 178. In at least one preferred embodiment, the label 212 and the exposed cover of the IFU 213 can be read without opening the header bag. In at least one preferred embodiment, the IFU 213 is place on the same side of the header bag as the top of the loaded, final mounting card packaging configuration. In at least one preferred embodiment, the IFU 213 rests over a lip perimeter of the mounting card packaging, which may provide a more stable top surface for stackability. In this case, the IFU footprint is preferably large enough that it covers at least a continuous part of the lip perimeter.

After the final assembly is sterilized in the header bag 178, it is ready for use. To open the sterilized header bag 178, the header 214 is peeled away from the clear polymer bag, and the kit is slid out of the resulting opening in the bag. Then, for a no-touch procedure, the caregiver then holds the handle of the forceps 101b and opens the CSR wrap by lifting the tail of the CSR wrap sticking out of the fold in the CSR wrap that the forceps were in. It is important to maintain sterility of the grabbing ends of the forceps and the inside of the CSR wrap 177. The CSR wrap is completely unwrapped to the configuration shown in FIG. 25, which in turn serves as the base for the sterile field. and its sterile contents. In the preferred embodiment, all of the necessary sterile components for the wound dressing are already on the CSR wrap in the mounting card packaging assembly. This reduces the risk of a potential breach in the sterile field, as no outside components need to be added. The only exception for the disclosed embodiment is that sterile saline may be needed, which is ideally poured using the standard, sterile pouring method into the saline container when needed.

After the CSR wrap is opened, the user can then use the first forceps to lift the left 186 and right 184 lips of the folded mounting card, as shown in FIG. 28. Then, in the preferred embodiment, the packaging falls flat due the gauge and material of the mounting card material, design of the sidewall folds, and weight of the components on the sidewalls, except for the sidewall with the instruction label, which falls to about 45-50 degrees for easy in-procedure visualization, as shown in FIG. 29. In the preferred embodiment, the second forceps 101a can be easily grasped and removed from the packaging without breaking the sterile barrier, as they may fall to an upright position at the user side of the card, as shown in FIG. 29.

The user can follow the instruction label 115 and/or start the procedure; if a no-touch procedure is being implemented, the user will use the forceps in each hand to manipulate the components in a sterile manner. The forceps are then required until the wound is occlusively sealed (i.e., after step "4" on the instruction label, shown in FIG. 16), unless the user provides their own sterile handling tools, such as sterile gloves.

In at least one preferred embodiment, features may be added in the card to aid in component removal with the forceps and/or by-hand. These may take the form of strategically placed holes 215 of FIG. 17A in the card to stick the forceps and/or finger(s). These features may be desirable to easily remove components that are hard to grasp and/or are locked into place with retaining features, and require a removal force. In FIG. 23, this concept is shown with a saline container 104 that is difficult to easily grasp with forceps, in order to provide the necessary removal force from the retention folds. Therefore, a hole 215 is placed at the edge of the container, in order to easily slip the forceps under the lip for easy pick-up. These assistive features (e.g., holes) may also be incorporated into other features on the card, such as component retention folds that may need to be manipulated for component removal.

During the procedure, any trash may be placed into the header bag, and when the procedure is over, any additional trash can be wrapped in the CSR wrap and placed in the header bag. This allows for easy and ambulatory clean-up. However, any disposal procedures of the care setting should always be followed, and any medical waste should be disposed of accordingly. In at least one embodiment, it is preferable that at least one of outside corners of the mounting card are rounded, that is, are shaped with a radius or other curvature instead of having a sharp angle, in order to increase the safety of the packaging and/or to prevent the card from puncturing any disposal container; it is more preferable that at least a majority of the outside corners are rounded, and it is even more preferable that all the outside corners are rounded.

Although specific features of the present invention are shown in some drawings and not in others, this is for convenience only, as each feature may be combined with any or all of the other features in accordance with the invention. While there have been shown, described, and pointed out fundamental novel features of the invention as applied to a preferred embodiment thereof, it will be understood that various omissions, substitutions, and changes in the form and details of the devices, packaging, and/or jigs illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A packaging system comprising:
   (i) a thin, planar sheet of material that is configured to be folded in a folding direction to have a base, a first sidewall and at least two other sidewalls in a final packaging configuration, the base being central to at least the first sidewall and the at least two other sidewalls in a planar, unfolded configuration, each sidewall having a top edge, a bottom edge and two opposite side edges in the final packaging configuration, at least one folding line being defined between the base and at least each of the at least three sidewalls in the final packaging configuration, the bottom edge of each sidewall being defined by one of the folding lines, the at least three sidewalls establishing at least a first pair of adjacent sidewalls in the final packaging configuration, and at least a first mounting feature being defined on at least the first sidewall; and
   (ii) a first medical device component and a second medical device component, wherein the first and the second medical device components are separate medical device components and wherein the first medical device component has a largest dimension along any axis of that component;
   wherein the final packaging configuration forms an enclosed volume that holds at least the first and the second medical device components, wherein the enclosed volume has a largest dimension along any axis of the enclosed volume and wherein the largest dimension of the enclosed volume is larger than the largest dimension of the first medical device component;
   wherein at least the first mounting feature secures at least the first medical device component onto at least the first sidewall; and
   wherein at least one of the first and/or the second medical device components is mounted onto at least one sidewall without being secured by any mounting feature at least one of at least partially integrated with the base and/or at least partially connected to the base when the planar sheet is folded into the final packaging configuration, and the first medical device component remains secured by at least the first mounting feature when the packaging system in the final packaging configuration is deployed in an unfolding direction to a display layout.

2. The system of claim 1 wherein at least the first mounting feature defined on at least the first sidewall (i) is integral with at least the first sidewall and (ii) includes at least one fold in at least the first sidewall within the top edge, the bottom edge and the two opposite side edges of the first sidewall in the final packaging configuration.

3. The system of claim 1 wherein additional features in the planar sheet temporarily hold the first pair of adjacent sidewalls together in the final packaging configuration, wherein each sidewall in the first pair of adjacent sidewalls in the final packaging configuration has an adjacent side edge, and wherein the additional features are not connected to the adjacent side edges.

4. The system of claim 1 wherein additional features in the planar sheet temporarily hold at least every other pair of adjacent sidewalls together when viewed around the base in a clockwise or counterclockwise direction in the final packaging configuration starting with a pair of sidewalls with the additional features, wherein each sidewall in the at least every other pair of adjacent sidewalls in the final packaging configuration has at least one adjacent side edge, and wherein the additional features do not include any interlocking feature connected to each corresponding pair of adjacent side edges.

5. The system of claim 1 wherein additional features in the planar sheet temporarily hold every pair of adjacent sidewalls together in the final packaging configuration, wherein each sidewall in the every pair of adjacent sidewalls in the final packaging configuration has at least one adjacent side edge, and wherein the additional features do not include any interlocking feature connected to any adjacent side edge.

6. The system of claim 1 wherein at least one of the first and/or the second medical device components is at least one component of at least one of NPWT (Negative Pressure Wound Therapy), wound cleaning, and/or chronic wound treatment.

7. The system of claim 1 wherein at least one feature in the final packaging configuration is disengaged by a user to activate packaging instructions facing the enclosed volume on at least one of the at least three sidewalls in the final packaging configuration.

8. The system of claim 1 wherein at least one feature in the final packaging configuration is disengaged by a user to achieve the display layout on a working surface by unfolding the final packaging configuration in the unfolding direction during deployment, and wherein at least the first and the second medical device components are arranged in a selected order in the display layout while the first medical device component remains secured by at least the first mounting feature.

9. The system of claim 1 wherein a perimeter is formed around a top border of the final packaging configuration when the planar sheet is folded into the final packaging configuration, and wherein at least one lip is defined around approximately the entire perimeter of the top border.

10. The system of claim 9 wherein the at least one lip is constructed of at least one lip feature defined on at least a portion of the top edge of at least one sidewall and a plurality of separate medical device components are mounted onto the at least one lip feature in the final packaging configuration without being secured by any mounting feature defined on the base when the planar sheet is folded into the final packaging configuration.

11. The system of claim 9 wherein the at least one lip is constructed of at least two lip features, wherein each of at least two separate sidewalls have at least one of the at least two lip features integral with at least a portion of the top edge, and wherein the at least one of the at least two lip features integral with at least a portion of the top edge of each of the at least two separate sidewalls are interlocked with each other in the final packaging configuration.

12. The system of claim 1 further including at least one separate sheet of material placed completely around the planar sheet after folding to constrain it and provide additional structural support in the final packaging configuration, wherein the at least one separate sheet of material is not adhered to the planar sheet of material in the final packaging configuration and wherein the at least one separate sheet of material is at least one planar wrap.

13. The system of claim 1 wherein the at least one of the first and/or the second medical device components is mounted onto the at least one sidewall without contacting the base when the planar sheet is folded into the final packaging configuration.

14. The system of claim 1 wherein the base has at least three outside edges in the final packaging configuration, and wherein no mounting features are in the planar sheet of material within any of the outside edges of the base in the final packaging configuration.

15. The system of claim 9 wherein the at least one lip is constructed of at least one lip feature defined on at least a portion of the top edge of at least one sidewall, wherein the at least one lip feature has at least one surface that faces the base when the planar sheet is folded into the final packaging configuration, wherein at least one separate medical device component is mounted onto the at least one surface of the at least one lip feature, and wherein the at least one separate medical device component mounted onto the at least one surface of the at least one lip feature (i) is held completely in the enclosed volume of the planar sheet when the planar sheet is folded into the final packaging configuration and (ii) is not secured by any mounting feature defined on the base when the planar sheet is folded into the final packaging configuration.

16. The system of claim 1 wherein at least one lip feature is defined on at least a portion of the top edge of at least one sidewall in the final packaging configuration, and wherein any lip feature defined on at least a portion of the top edge of any sidewall in the final packaging configuration covers less than a majority of the base.

17. The system of claim 1 wherein the at least one of the first and/or the second medical device components is mounted onto the at least one sidewall and exerts a force on the base when the planar sheet is folded into the final packaging configuration.

18. The system of claim 1 further including at least two sterile components capable of manipulating objects, wherein at least one of the sterile components is forceps or tweezers.

19. The system of claim 8 wherein at least one post-disengaged sidewall has at least one of (1) a stiffness of the at least one folding line and/or (2) a weight of the at least one post-disengaged sidewall and anything connected to the at least one post-disengaged sidewall that generates a force in the unfolding direction of the at least one post-disengaged sidewall when the at least one feature in the final packaging configuration is disengaged, and wherein the force activates the at least one post-disengaged sidewall to unfold onto the working surface to achieve the display layout.

20. The system of claim 1 wherein the first pair of adjacent sidewalls includes the first sidewall and at least one of the other sidewalls wherein the planar sheet includes at least a second mounting feature being defined on at least that other sidewall, wherein at least the second mounting feature secures at least the second medical device component onto at least that other sidewall in the final packaging configuration.

21. The system of claim 9 further including a separate instructions for use component, wherein the separate instructions for use component is a physically separate component from the planar sheet and wherein the separate instructions for use component covers at least a portion of the at least one lip in the final packaging configuration and forms a top planar surface.

22. The system of claim 9 wherein at least the majority of the at least one lip is not connected to the base within the bottom edges of all of the sidewalls by the planar sheet of material in the final packaging configuration, and wherein the at least one lip is constructed of at least two lip features, wherein each of at least two adjacent sidewalls have at least one of the at least two lip features integral with at least a portion of the top edge, and wherein the at least one of the at least two lip features integral with at least a portion of the top edge of each of the at least two adjacent sidewalls overlap each other in the final packaging configuration.

23. The system of claim 1 wherein at least one additional feature is in the planar sheet and wherein the at least one additional feature in the planar sheet temporarily holds only one pair of adjacent sidewalls together in the final packaging configuration, and no other pair of adjacent sidewalls is temporarily held together in the final packaging configuration by any additional feature in the planar sheet.

24. The system of claim 1 wherein additional features are in the planar sheet and wherein the additional features in the planar sheet temporarily hold only every other pair of adjacent sidewalls together when viewed around the base in a clockwise or counterclockwise direction in the final packaging configuration starting with a pair of sidewalls with the additional features, and no other pair of adjacent sidewalls is temporarily held together in the final packaging configuration by any additional feature in the planar sheet.

25. The system of claim 5 wherein at least one lip is defined around at least a majority of a top border in the final packaging configuration, wherein the at least one lip is constructed of at least one lip feature integral with at least a portion of the top edge of each sidewall, wherein at least one of the additional features is defined on the at least one lip feature, and wherein each pair of adjacent sidewalls are temporarily held together in the final packaging configuration by at least one of the additional features defined on the at least one lip feature integral with at least the portion of the top edge of each corresponding adjacent sidewall.

26. The system of claim 1 wherein a working surface includes a table that is flat and wherein at least a portion of at least one medical device component mounted onto at least one sidewall is vertically above at least a portion of at least one separate medical device component on the base in the final packaging configuration when the base of the final packaging configuration is placed on the table.

27. The system of claim 1 wherein a working surface includes a table that is flat and wherein at least a majority of the first medical device component is vertically above at least a portion of at least one separate medical device component on the base in the final packaging configuration when the base of the final packaging configuration is placed on the table.

* * * * *